US011837339B2

(12) United States Patent
Chen et al.

(10) Patent No.: US 11,837,339 B2
(45) Date of Patent: Dec. 5, 2023

(54) ANALYTE METER

(71) Applicant: Ascensia Diabetes Care Holdings AG, Basel (CH)

(72) Inventors: Jun Chen, Warren, NJ (US); Harris Lieber, White Plains, NY (US); Erik Nelson, Ridgefield, CT (US); Jeffery S. Reynolds, New Fairfield, CT (US); Kevin Curran, Wayne, NJ (US); Aseem Mehta, Mountain Lakes, NJ (US); Dawn Rountree, Derby, CT (US)

(73) Assignee: Ascensia Diabetes Care Holdings AG, Basel (CH)

( * ) Notice: Subject to any disclaimer, the term of this patent is extended or adjusted under 35 U.S.C. 154(b) by 277 days.

(21) Appl. No.: 16/908,192

(22) Filed: Jun. 22, 2020

(65) Prior Publication Data

US 2020/0365240 A1    Nov. 19, 2020

Related U.S. Application Data

(63) Continuation of application No. 15/525,888, filed as application No. PCT/US2015/060653 on Nov. 13, 2015, now Pat. No. 10,714,212.

(Continued)

(51) Int. Cl.
*G16H 10/40* (2018.01)
*A61B 5/00* (2006.01)
(Continued)

(52) U.S. Cl.
CPC .......... *G16H 10/40* (2018.01); *A61B 5/0015* (2013.01); *A61B 5/14532* (2013.01);
(Continued)

(58) Field of Classification Search
CPC ...... G16H 10/40; G16H 40/63; A61B 5/0015; A61B 5/14532; A61B 5/742; A61B 5/746;
(Continued)

(56) References Cited

U.S. PATENT DOCUMENTS 8,427,817 B2    4/2013    Lewis
D742,524 S    11/2015    Yao
(Continued)

FOREIGN PATENT DOCUMENTS

JP    2013-544550 A    12/2014

OTHER PUBLICATIONS

OneTouch LifeSean, inc; "One Touch Veriosync Blood Glucose Monitoring System Owner's Booklet": Jul. 1, 2012, Rev. Jun. 2014) (Year: 2014).*

(Continued)

*Primary Examiner* — Dennis White
(74) *Attorney, Agent, or Firm* — ERISE IP, P.A.

(57) ABSTRACT

A portable data-management system based on an analyte testing device which communicates wirelessly with a mobile device. The mobile device runs an application to manage and analyze data obtained by the analyte testing device. The mobile device may assist the user in displaying testing data, identifying patterns to assist healthy behavior or issue warnings based on the collected data. The mobile device may be connected to a network to store user health data for use by other parties.

18 Claims, 13 Drawing Sheets
(12 of 13 Drawing Sheet(s) Filed in Color)

Related U.S. Application Data

(60) Provisional application No. 62/080,067, filed on Nov. 14, 2014.

(51) Int. Cl.
    *G16H 40/63*     (2018.01)
    *A61B 5/145*     (2006.01)
    *C12Q 1/54*     (2006.01)
    *G01N 33/66*     (2006.01)
    *A61B 5/1486*     (2006.01)

(52) U.S. Cl.
    CPC .............. *A61B 5/742* (2013.01); *A61B 5/746* (2013.01); *C12Q 1/54* (2013.01); *G01N 33/66* (2013.01); *G16H 40/63* (2018.01); *A61B 5/1486* (2013.01); *A61B 5/14546* (2013.01); *A61B 5/7275* (2013.01)

(58) Field of Classification Search
    CPC . A61B 5/14546; A61B 5/1486; A61B 5/7275; C12Q 1/54; G01N 33/66
    See application file for complete search history.

(56) References Cited

U.S. PATENT DOCUMENTS

| | | | |
|---|---|---|---|
| 2007/0253021 A1* | 11/2007 | Mehta | H04L 61/5038 382/128 |
| 2011/0193704 A1* | 8/2011 | Harper | A61B 5/14 340/573.1 |
| 2011/0201911 A1 | 8/2011 | Johnson | |
| 2012/0274443 A1 | 11/2012 | Kai | |
| 2013/0059541 A1 | 3/2013 | Sloan | |
| 2014/0081662 A1* | 3/2014 | Bradrick | A61B 5/14503 705/2 |
| 2014/0235171 A1* | 8/2014 | Molettiere | A61B 5/486 455/41.2 |
| 2014/0322815 A1 | 10/2014 | Carlsgaard | |
| 2017/0205553 A1 | 7/2017 | Prais | |

OTHER PUBLICATIONS

International Search Report and Written Opinion in International Application No. PCT/USZOlS/06053, dated Feb. 25, 2016 (14 pages).

LifeSean, Inc; "OneTouch Veriosyne Blood Glucose Monitoring System Owner's Booklet," Jul. 1, 2012, Rev. Jun. 2014; XP55124924; (116 pages) retrieved from http://www.onetouch.com/support/products/veriosync.

LifeScan, Inc. et al., "App Owner's Booklet Instructions for use with the OneTouch VerioSync Blood Glucose Monitoring System and the iPhone, iPod touch and iPad," pp. 1-122; Jul. 1, 2012; XP055251310; retrieved from https://web.archive.org/web/20140308053522/http://www.onetouch.com/sites/default/files/file/OneTouch_Reveal_Mobile_App_Owners_Booklet_web.pdf.

"Contour Link Wireless Blood Glucose Monitoring System User Guide," pp. 1-49; copyright 2012, Rev. Apr. 2012 (28 pages).

Bayer HealthCare LLC; "Contour Next USB Blood Glucose Monitoring System User Guide," copyright 2012, Rev. Oct. 2012 (47 pages).

Aseensia Diabetes Care US, Inc. "Bayer Contour Blood Glucose Monitoring System User Guide," copyright 2006, Rev. Nov. 2006 (53 pages).

OneTouch Reveal, (LifeScan, Inc.; "OneTouch Reveal App, Owner's Booklet Instructions for use"; Rev. Apr. 2014; (124 pages) retrieved from http://origin-www.onetouch.com/sites/default/files/pdf/OneTouch_Reveal_mobile%20app_Owners%20Booklet_%2006773001B_OTR_OB_US_en_zug_R1_Ful_web.pdf (2014).

Elecom K.K., "Just touch to pair, NFC support for super easy setup! Ultra-slim Bluetooth headset for cable-free conversation and music is now available," Published online May 21, 2013, Retrieved from the Internet <https://www.elecom.co.jp/news/201305/lbt-mphs3 10m/index.html/> (2 pages).

LifeScan, Inc., "ONETOUCH VerioSyne Blood Glucose Monitoring System Owner's Booklet," Published online Jun. 2014, Retrieved from the Internet <https://www.onetouch.com/sites/onetouch_us/files/veriosyncmeter.pdf/> (28 pages).

Japanese Patent Application 2020-214949, Office Action dated Mar. 29, 2022.

ACCU-CHEK(R) Inform II Blood Glucose Monitoring System Operators Mannual, [online], Mar. 2013, Internet<URL: https://diagnostics.roche.com/content/dam/diagnostics/us/en/products/a/accu-chek-inform-ii/toolkit/05234646002_ACI2_OpsMan.pdf>, [Retrieved on Mar. 22, 2022], (p. 63,64).

OneTouch Verio Blood Glucose Monitoring System Owner's Booklet, Jul. 2014.

European Patent Application 19218031.3 Minutes from Examiner Meeting held Feb. 10, 2023.

European Patent Application 19218031.3 Communication under Rule 71(3) EPC Intent to Grant, dated Apr. 25, 2023.

\* cited by examiner

ANALYTE METER

CROSS-REFERENCE TO RELATED APPLICATION

This application claims priority to U.S. Provisional Patent Application No. 62/080,067, filed Nov. 14, 2014, which is hereby incorporated by reference herein in its entirety.

TECHNICAL FIELD

The present invention relates generally to a method and system for managing health data via a health meter and a mobile device. More specifically, the present invention relates to a portable system that manages and displays information associated with the health of an individual, such as measurements of an analyte in a bodily fluid made by a testing device, on a mobile device.

BACKGROUND

The quantitative determination of analytes in body fluids is of great importance in the diagnosis and maintenance of certain physiological conditions. For example, individuals with diabetes frequently check the glucose level in their bodily fluids. The results of such tests can be used to regulate the glucose intake in their diets and/or to determine whether insulin or other medication needs to be administered.

Diagnostic systems, such as blood-glucose monitoring systems, may employ an instrument, such as a meter, to calculate the glucose concentration value in a fluid sample from an individual. Such instruments operate by measuring an output, such as current or light, from a reaction with the glucose in the sample. The test results typically are displayed and stored by the meter. Basic systems allow the user to access the test results directly from the meter via a display and a keypad or other interactive component.

Since measurements for individuals with diabetes is crucial, it is imperative that instruments are available that allow convenient readings of diagnostic results. For example, specialized systems are available, but these systems are expensive. Further, information relating to measurements is helpful for a user, if the information is readily accessible, but specialized testing devices are often not designed to provide helpful information to a user.

Thus, there is a need for a system that allows wireless connectivity between an analyte meter to a ubiquitous device executing analysis software such as a smart mobile device. There is a need for a system that allows accessing and downloading reliable patient data and identifying trends to reduce time spent advising patients. There is a need for a system that allows a user ease of access and ability to interact with health-related applications, allowing for a more integrated and natural fit to a user's lifestyle.

SUMMARY

A system for convenient analysis and management of health reading data is disclosed. A testing device or meter is operative to test a fluid from a user. The testing device or meter communicates data to a mobile user device such as a smart phone via a wireless link to pair the testing device with the mobile user device. The mobile user device runs a data analysis and management application, which may be loaded on the mobile device from a network cloud server. The data analysis and management application allows a display of testing data from the testing device, as well as other readings taken by the testing device or other testing devices paired with the mobile device. The application on the mobile device may send the data to a cloud server via the network for health care purposes. The application may provide alerts for a user to perform testing using the testing device based on criteria such as times, locations or meals. The application may analyze the data and determine patterns of behavior for the user. The application may also set warnings when readings fall outside normal parameters.

The application may monitor and display different configurations of the testing device and allow a user to control certain functions of the testing device. The application allows a user to enter information such as notes, pictures, food descriptions, or medication to be associated with readings. The mobile device 130 may show different formats of data depending on the orientation of the device.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

BRIEF DESCRIPTION OF THE DRAWINGS

This patent or application file contains at least one drawing executed in color. Copies of this patent or patent application publication with color drawings will be provided by the Office upon request and payment of the necessary fee.

Exemplary embodiments are illustrated in referenced figures. It is intended that the embodiments and figures disclosed herein are to be considered illustrative rather than restrictive.

DESCRIPTION OF ILLUSTRATED EMBODIMENTS

Figure 1:
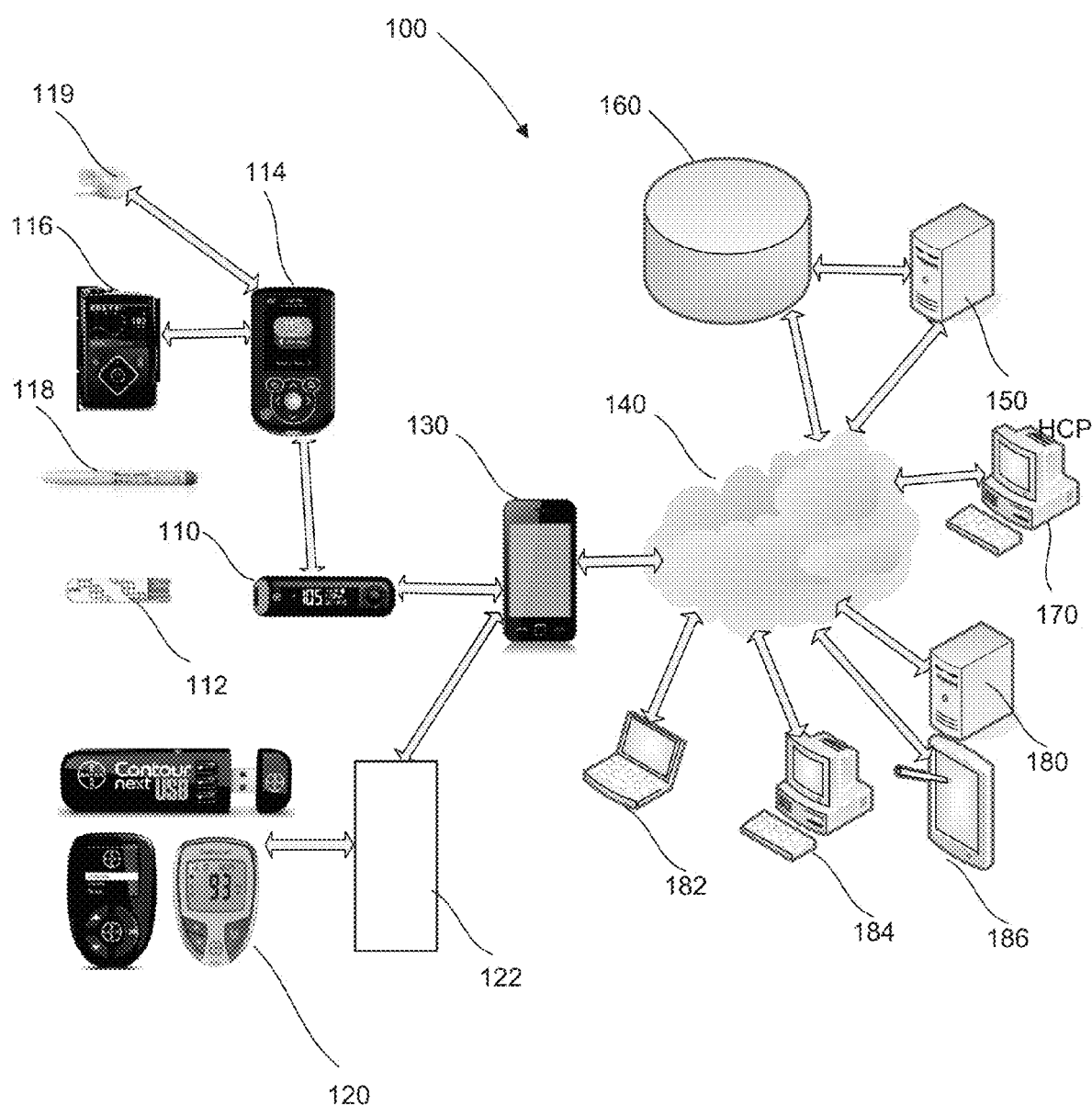
FIG. 1 illustrates a data collection system including a mobile device in communication with a meter or testing device for analyte testing.

FIG. 1 shows a system 100 for collecting testing data for different users for health conditions such as diabetes. The system 100 includes a meter testing device 110 which is in wireless communication with a mobile device 130. In this example, the testing device 110 allows testing of analytes as will be explained below. The testing device 110 is paired with a mobile device 130 via a wireless link. Once the pairing is established, the testing data from the testing device 110 are passed to the mobile device 130, which runs software that performs detailed analysis of the data, allows management of the data, and provides other relevant information in a format that may be readily understood by a user of the mobile device 130. The software thus performs data management relating to test results for the user of the mobile device 130.

In this example, a fluid sample (e.g., blood or interstitial fluid) may be obtained via a test sensor 112 that is configured to be inserted into the testing device 110. The testing device 110 may also communicate with a control meter 114. The control meter is configured to control an insulin pump 116. A user may use an insulin pen 118 in conjunction with the insulin pump 116 and the control meter 114. A continuous glucose monitor (CGM) sensor 119 communicates with the control meter 114 to transmit glucose data. Other meters or testing devices 120, besides the testing device 110, may also analyze fluid samples from the test sensor 112 and interface with an interface device 122 to communicate test data to the mobile device 130.

The mobile device 130 performs data analysis on data obtained from the testing device 110, as will be explained below. The mobile device 130 allows communication with a wide area network such as the Internet 140. The system 100 includes a server 150 that is coupled to a database 160. The server 150 maintains patient data in the database 160. Other users, such as health care providers, may have access to patient data in the database 160 via a network-connected device such as a personal computer 170. There are multiple users who may access the server 150 via mobile devices such as the mobile device 130.

For example, the server 150 may be part of a centralized health care system that provides further processing or storage of data collected by the mobile device 130. The centralized health care system may provide a web-based or a client-server based front end to data-management software running on the mobile device 130. Additionally or alternatively, the data may be shared with health care providers (HCPs). Accordingly, to transfer data from the mobile device 130 to the server 150, the mobile device 130 may connect directly via an interface, for example, to a wireless network or a Wi-Fi hotspot to the network 140. Data encryption and authentication procedures may be employed to ensure data security. The mobile device 130 detects the presence of a wireless network or a Wi-Fi hotspot and automatically transfers data to the server 150 through a background process. Alternatively, the mobile device 130 may alert the user that access to the server 150 is available, and the user can initiate data transfer if desired.

The server 150 may be used for a variety of heath care functions. For example, the data may be shared with a health care professional for more effective visits. The data may be used for health monitoring of a user or remote patient care. The data may be used for life style programs. As will be explained below, the mobile device 130 may include other applications such as activity or fitness monitor applications that may interface with the user data. The data may be used for motivational support tools from persons with diabetes. Other health care providers may receive selected data via other devices such as a server 180, a laptop 182, a personal computer 184, a tablet 186, or any other computing device that allows access to data from the database 160 for other health care services such as monitoring, marketing and provision of services and products.

Figure 2A:
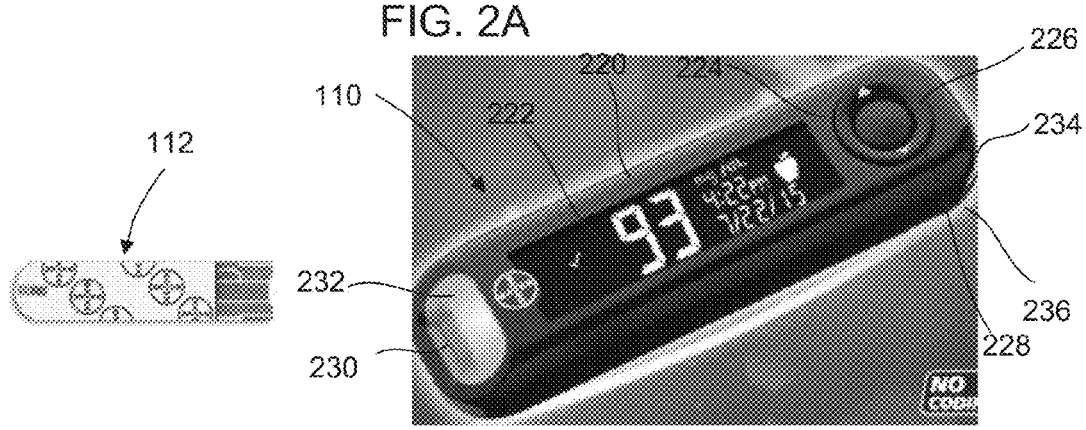
FIG. 2A illustrates a top view of a test sensor and a perspective view of a meter in the system of FIG. 1.

Referring to FIG. 2A, a top view of the testing meter or testing device 110 and a perspective view of the test sensor 112 is illustrated. The test sensor 112 is configured to receive a fluid sample which is analyzed using the testing device 110. Analytes that may be analyzed include glucose, lipid profiles (e.g., cholesterol, triglycerides, LDL and HDL), microalbumin, hemoglobin $A1_C$, fructose, lactate, or bilirubin. The analytes may be in, for example, a whole blood sample, a blood serum sample, a blood plasma sample, other body fluids like ISF (interstitial fluid) and urine, and non-body fluids.

The test sensor 112 includes a fluid-receiving area. The fluid-receiving area contains a reagent that reacts with a fluid sample to indicate the analyte concentration of the fluid sample. For example, the fluid-receiving area may receive a fluid sample, such as a blood sample. The fluid-receiving area may also receive a liquid-control solution. The liquid-control solution contains a control marker (also referred to as an internal reference) and is used to check that the testing device 110 and test sensor 112 are functioning correctly. The control marker generates a distinctive current profile, which is detected using a detection algorithm run by the testing device 110. By having a distinctive current profile, the testing device 110 can automatically distinguish a control test from an analyte-fluid test (e.g., a glucose blood sample).

Some commercially available test sensors that may be used include those that are available commercially from Bayer HealthCare LLC (Whippany, New Jersey). These test sensors include, but are not limited to, those used in the Ascensia® CONTOUR® blood glucose monitoring system, the CONTOUR® LINK blood glucose monitoring system, CONTOUR® NEXT USB blood glucose monitoring system, the Ascensia® BREEZE® and BREEZE®2 blood glucose monitoring system. Other test sensors, in addition to the ones listed above, may be incorporated into the methods and systems of the present disclosure.

The test sensor may be an electrochemical test sensor such as the sensor 112. The electrochemical test sensor 112 typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. In general, the enzyme is selected to react with the desired analyte or analytes to be tested so as to assist in determining an analyte concentration of a fluid sample. If the concentration of another analyte is to be determined, an appropriate enzyme is selected to react with the analyte.

The reagent also typically includes a mediator that assists in transferring electrons between the analyte and the electrodes. The reagent may include binders that hold the enzyme and mediator together, other inert ingredients, surfactants, polymers (e.g., cellulose polymers) buffers or combinations thereof.

The testing device 110 of FIG. 2A includes a user interface 220, which includes a display 222 and a user-input device 224. The display 222 typically displays information regarding the test results, the testing procedure and/or information in response to signals input by the user, including text and images. The display 222 may be a graphic liquid crystal display (LCD), an organic light-emitting diode (OLED), segment LCD, or the like. The user-input device 224 allows the user to interact with the testing device 110 and may include push buttons, soft keys, a scroll wheel, touch-screen elements, or any combination thereof. In this example, the user input device 224 includes a circular control 226 to navigate around the display 222 and a push button 228 to activate selected functions on the display 222.

The display 222 may be a high-resolution, rich viewing display, which may present both static and moving text and images to the user. However, other types of displays, including, for example, lower resolution, monochromatic LCD displays, may be employed. In general, a range of display types, from a low-cost basic display to a fully functional display, may be employed. The display 222 may be of any suitable size. In some cases, the display 222 may cover one entire side of the testing device 110. Moreover, the display 222 may include a touchscreen. In addition, the user interface 220 may provide advanced graphical user display and audio capabilities available directly on the testing device 110 or via a communications interface with the testing device 110.

The testing device 110 includes a test sensor port or opening 230 for receiving the sensor 112. An illumination panel 232 is disposed around the test strip port 230 to assist in guiding the sensor 112 to be inserted in the test strip port 230. A charging port 234 allows the testing device 110 to be charged. In this example, the charging port 234 also allows test data to be downloaded on a computer connection such as a USB port. The testing device 110 may have a power source such as a rechargeable battery, which may be recharged via the connection with a power supply. For example, power may be transferred via a USB connection between a power source and the testing device 110.

A wireless interface 236 allows transmission of test data wirelessly from the testing device 110. The wireless transmission protocol may be Bluetooth, but other protocols may be used. The illumination panel 232 may emit different colored light to assist the user and communicate information to the user. For example, the illumination panel 232 may emit white light to assist the user to mate the testing sensor 112 to the testing device 110. The illumination panel 232 may emit blue light to indicate that there is Bluetooth pairing with a mobile device such as the mobile device 130 in FIG. 1. The illumination panel 232 may emit a green color to indicate the reading is within normal parameters. The illumination panel 232 may emit a red color to indicate that the reading is below normal parameters indicating a hypoglycemic condition. The illumination panel 232 may emit an orange color to indicate the reading is above normal parameters indicating a hyperglycemic condition. It is contemplated that other additional colors may be used to indicate operation or readings to be communicated to the user.

As described previously, the testing device 110 employs at least one controller that typically executes programmed instructions, as well as the user interface 220, which includes the display 222 to present information to the user, and input device 224, such as pushbuttons, soft keys, a scroll wheel, touch screen elements, or any combination thereof, to enable interaction with the user.

Figure 2B:
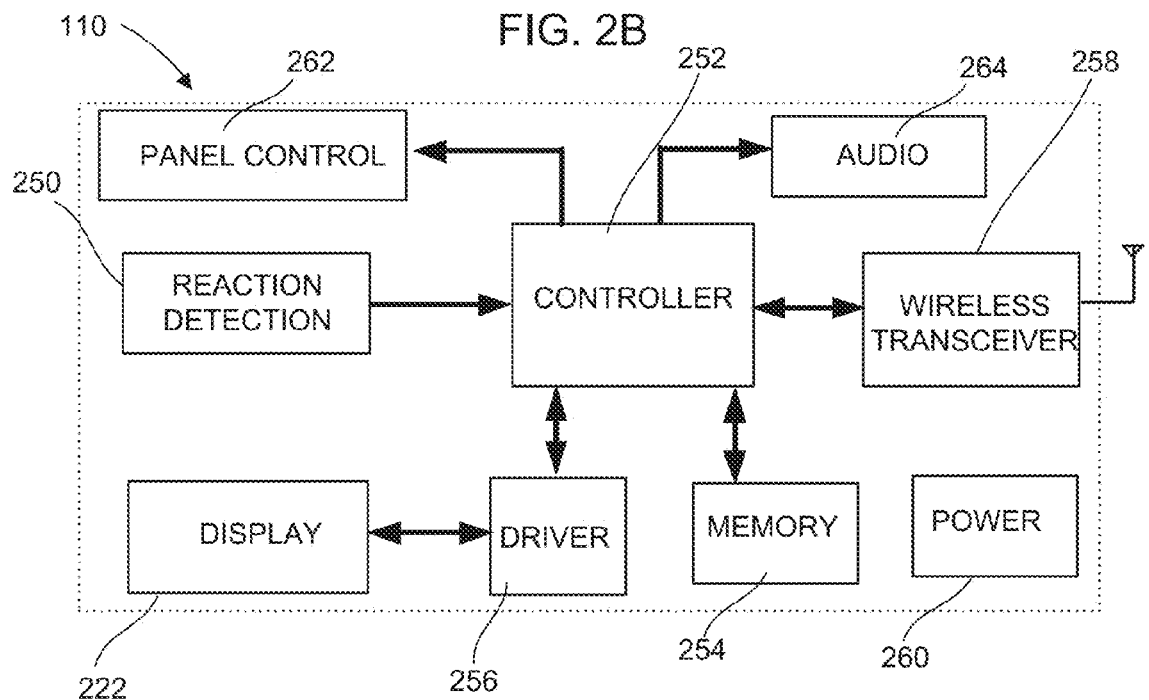
FIG. 2B illustrates a block diagram of the electronic components of the meter in FIG. 1.

As shown in FIG. 2B, the testing device 110 includes a reaction-detection system 250 for measuring the analyte concentration for the sample collected by the test sensor 112.

As described above, the reaction-detection system 250 may include contacts for the electrodes to detect the electrochemical reaction for an electrochemical test sensor 112 when inserted in the test sensor port 230. Alternatively, the reaction-detection system 250 may include an optical detector to detect the chromatic or reflectance results of a reaction for an optical test sensor. To calculate the actual analyte concentration from the electrochemical or optically-measured reaction measured by the reaction-detection system and to generally control the procedure for testing the sample, the testing device 110 employs at least one controller 252, which typically executes programmed instructions according to a measurement algorithm. Data processed by the controller 252 may be stored in a memory element 254.

The controller 252 is coupled to a display driver 256 that drives the display 222 in FIG. 2A. The controller 252 is coupled to a wireless transceiver 258. In this example, the wireless transceiver 258 is a Bluetooth transceiver for pairing with a mobile device such as the mobile device 130 in FIG. 1. The testing device 110 also includes a power source 260, which in this example is rechargeable battery, which may be charged via the charging port 234. The controller 252 also controls the color emitted by the illumination panel 232 via a panel control 262. The controller 252 also activates an audio output 264 that may be a beeping sound to indicate a successful or unsuccessful test, but other sounds may be used.

Figure 2C:
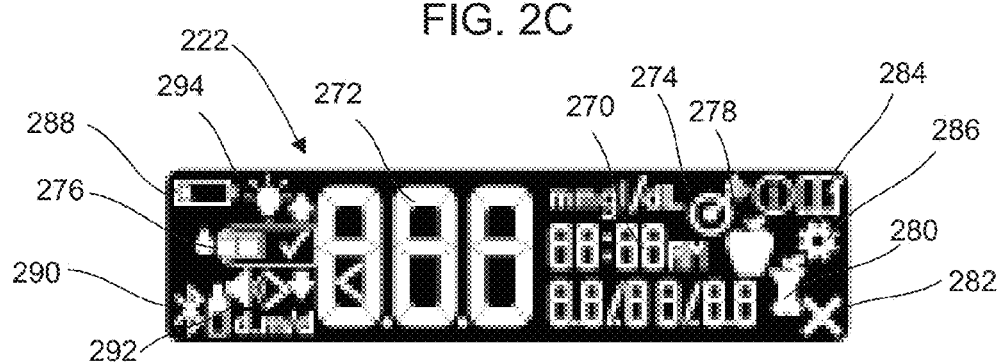
FIG. 2C illustrates a display of the meter in FIG. 2A.

FIG. 2C illustrates the display 222 in more detail. The display 222 includes a date and time 270, and a data reading 272. The data reading 272 is the measured blood glucose concentration. As will be explained below, marker icons indicate the conditions of the testing, which in this example may display different icons for pre-meal, post-meal and no meal. Of course other icons may be used. The display 222 may display a target range for different conditions such as before meal and after meal that may be adjusted using the application on the mobile device 130 as will be explained below. The input device 224 may be used to select a condition and corresponding target range. The target range may be selected by selecting a target icon 274.

In operation, the testing device 110 may be activated by either inserting a test sensor such as the test sensor 112 in the test sensor port 232 or holding the button 228. A testing icon 276 indicates that the test sensor 112 has been inserted. The user then inserts a drop of blood in the test sensor 112. The testing device 110 will make an audio indication if there is not enough blood in the test sensor 112. After a reading, the user may mark the reading by selecting one of the marker icons 278 or 280. In this example, there is a pre-meal marker 278 and a post-meal marker 280. A no-mark icon 282 may be selected if the user does not wish to mark the reading. As explained above, the data reading 272 shows the blood glucose concentration of the tested sample. Additional indicators in terms of a check mark and arrows appear in the reading 272 to indicate whether the reading is within the target range, above the target range, or below the target range. As explained above, the illuminated panel 232 will also change colors depending on the value of the reading in comparison with the target range. The display 222 may also display "HI" or "LO" to indicate exceptionally high or low blood glucose readings, possibly with an appropriate audio signal to warn the user of the condition. The controller 252 may activate the audio output 264 to warn the user of the unusual condition.

A logbook icon 284 allows a user to display an entry of a predetermined number of past readings taken by the test sensor 112. In this example, 800 readings are stored in the logbook by the testing device 110, but more or less readings may be stored in the logbook. The reading value, time, and date will be displayed for each entry. The circular control 226 may be used to scroll up and down entries when the logbook icon 284 is selected. A settings icon 286 allows a user to change settings on the display 222. The display 222 includes a battery low indicator 288 indicating a low battery and a Bluetooth symbol 290 indicating Bluetooth communication. A sound icon 292 allows a user to turn the audio on and off. The display 222 may display an error code indicating the testing device 110 is not functioning properly. A light panel icon 294 allows the user to activate and deactivate the illuminated panel 232.

Figure 3:
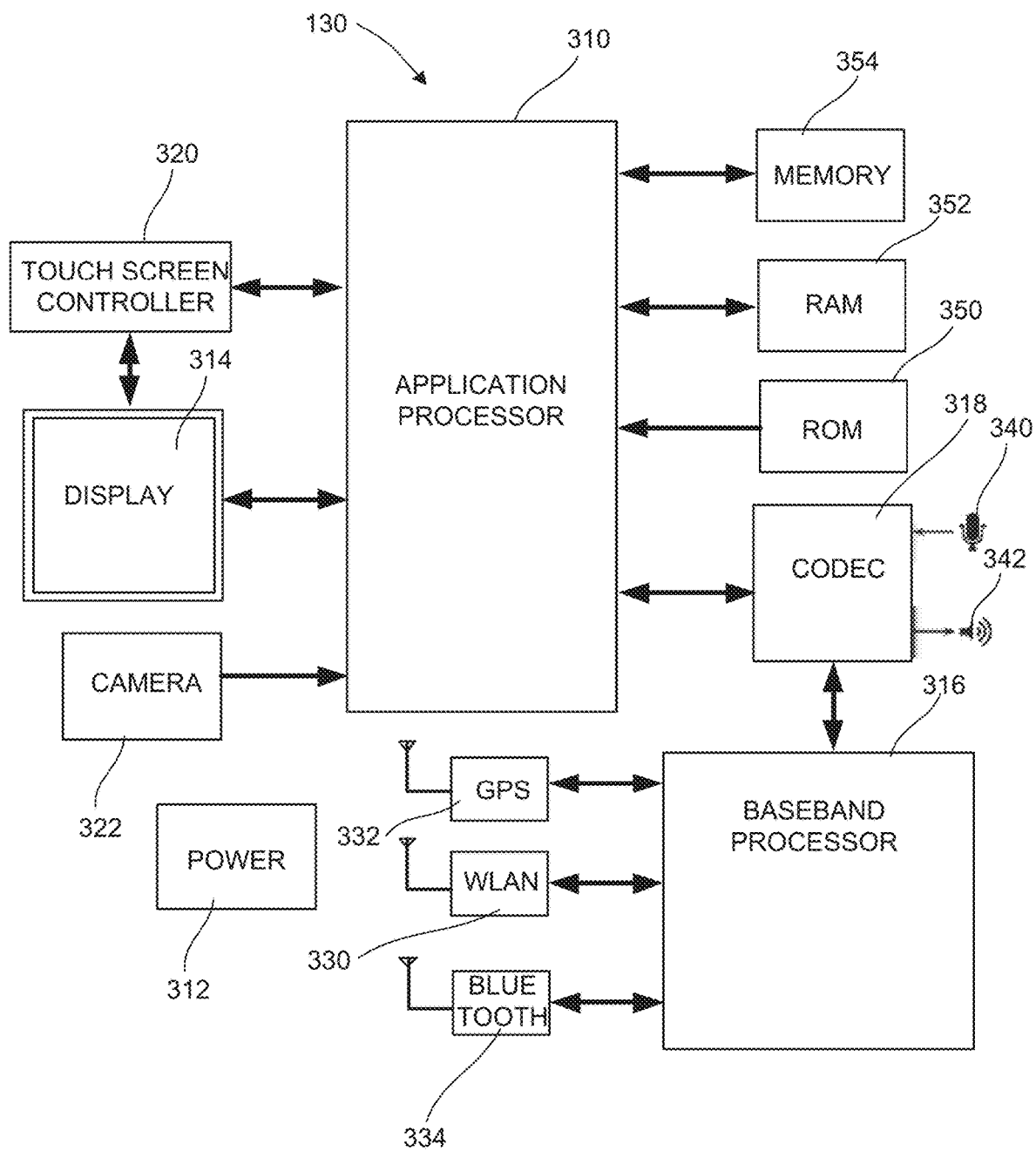
FIG. 3 illustrates a block diagram of a mobile device that includes an analysis program that displays relevant information relating to the results of analyte testing data transmitted wirelessly from the meter in FIG. 1.

FIG. 3 shows a block diagram of the mobile device 130 that communicates with the testing device 110 in FIG. 1 and runs the application described below for analyzing and managing analyte test data. In this example, the mobile device 130 may be virtually any preferably mobile computing device that is configured to send and receive information over a wireless communication medium such as Bluetooth. The mobile device 130 may be web-enabled and may run browser software for the presentation of web pages to the user. Such mobile user devices may include portable devices such as cellular telephones, smart-phones, display pagers, radio frequency (RF) devices, infrared (IR) devices, global positioning devices (GPS), Personal Digital Assistants (PDAs), handheld computers, wearable computers, tablet computers, integrated devices combining one or more of the preceding devices, and the like. Other Bluetooth-capable devices such as a lap top computer, a desk top computer, a work station or other computer may also be used to analyze data from and communicate with the testing device 110. The mobile devices may include multiprocessor systems, microprocessor-based, or programmable consumer electronics, and the like. As such, user devices running the application described below may range widely in terms of capabilities and features.

As exampled below, the web-enabled user devices may include a browser application enabled to receive and to send wireless application protocol messages (WAP), and/or wired application messages, and the like. In one example, the browser application is enabled to employ HyperText Markup Language (HTML), Dynamic HTML, Handheld Device Markup Language (HDML), Wireless Markup Language (WML), WMLScript, JavaScript, EXtensible HTML (xHTML), Compact HTML (CHTML), and the like, to display and/or send digital information.

The user devices may also include at least one client application that is configured to receive control data and/or content from another computing device via a network transmission. The client application may include a capability to provide and receive textual content, graphical content, video content, audio content, and the like. Moreover, the user devices may be further configured to communicate and/or receive a message, such as through a Short Message Service (SMS), direct messaging (e.g., Twitter), e-mail, Multimedia Message Service (MMS), instant messaging (IM), internet relay chat (IRC), mIRC, Jabber, Enhanced Messaging Service (EMS), text messaging, Smart Messaging, Over the Air (OTA) messaging, or the like, between or with another computing device, and the like.

The network 140 in FIG. 1 is configured to allow communications between one computing device with another computing device. The network 140 may be enabled to employ any form of computer readable media for communicating information from one electronic device to another. On an interconnected set of LANs, including those based on differing architectures and protocols, a router and/or gateway device acts as a link between LANs, enabling messages to be sent between computing devices. Also, communication links within LANs typically include twisted wire pair or coaxial cable, while communication links between networks may utilize analog telephone lines; full or fractional dedicated digital lines including T1, T2, T3, and T4; Integrated Services Digital Networks (ISDNs); Digital Subscriber Lines (DSLs); wireless links including satellite links; or other communication links known to those of ordinary skill in the art. Furthermore, remote computers and other related electronic devices can be remotely connected to either LANs or WANs via a modem and temporary telephone link.

The network 140 may further include any of a variety of wireless sub-networks that may further overlay stand-alone ad-hoc networks, and the like, to provide an infrastructure-oriented connection. Such sub-networks may include mesh networks, Wireless LAN (WLAN) networks, cellular networks, and the like. The network 140 may also include an autonomous system of terminals, gateways, routers, and the like connected by wireless radio links or wireless transceivers. These connectors may be configured to move freely and randomly and organize themselves arbitrarily, such that the topology of the network 108 may change rapidly and arbitrarily.

The network 140 may further employ a plurality of access technologies including 2nd (2G), 2.5, 3rd (3G), 4th (4G) generation radio access for cellular systems; WLAN; Wireless Router (WR) mesh; and the like. Access technologies such as 2G, 3G, 4G, and future access networks may enable wide area coverage for mobile devices, with various degrees of mobility. For example, the network 140 may enable a radio connection through a radio network access such as Global System for Mobile communication (GSM), General Packet Radio Services (GPRS), Enhanced Data GSM Environment (EDGE), Wideband Code Division Multiple Access (WCDMA), CDMA1100, and the like. The network 140 may also be constructed for use with various other wired and wireless communication protocols, including TCP/IP, UDP, SIP, SMS, RTP, WAP, CDMA, TDMA, EDGE, UMTS, GPRS, GSM, UWB, WiMax, IEEE 802.11x, and the like. In essence, the network 140 may include virtually any wired and/or wireless communication mechanisms by which information may travel between one computing device and another computing device, network, and the like.

FIG. 3 is a block diagram of the components of a mobile device such as the mobile device 130 in FIG. 1. The mobile device 130 includes an application processor 310, a power source 312, a display 314, a baseband processor 316, and a CODEC 318. In this example, the display 314 is an LCD touch screen that allows the user to control the applications run by the application processor 310 via touch inputs as well as view graphics generated by the application processor 310. The display 314 is controlled by a touch screen controller 320. The application processor 310 may be coupled to various devices such as a camera 322 and other interfaces such as a communication port, etc.

The baseband processor 316 receives signals from a network transmitter receiver 330 allowing communications with the network 140 in FIG. 1, a geo-referencing receiver 332 that allows the reception of positioning data to determine the location of the mobile device 130, and a Bluetooth receiver 334 that allows communication with Bluetooth-enabled devices such as the testing device 110. The baseband processor 316 processes in the signals and is coupled to the CODEC 318, which converts the signals for use by the application processor 310. The CODEC 318 also decodes audio signals received by a microphone 340 and encodes data signals for output by a speaker 342 for functions such as a telephone application run by the applications processor 310. It is contemplated that other audio devices such as a headset may be coupled through the CODEC 318.

The processors 310, 316 may be conveniently implemented using one or more general purpose computer systems, microprocessors, digital signal processors, microcontrollers, application specific integrated circuits (ASIC), programmable logic devices (PLD), field programmable logic devices (FPLD), field programmable gate arrays (FPGA), and the like, programmed according to the teachings as described and illustrated herein, as will be appreciated by those skilled in the computer, software, and networking arts.

The operating system software and other applications are stored on read only memory (ROM) 350, random access memory (RAM) 352 and a memory storage device 354 for access by the applications processor 310. In this example, the memory storage device 354 is flash memory, but other memory devices may be used. The applications stored on the memory storage device 354 include the emotional score data collection and broadcast application, which creates interface graphics on the display and interfaces with a browsing application. It is contemplated that other forms of applications may incorporate the principles explained below. In this example, the analysis application may be preloaded on the mobile device 130, or may be offered as an application that may be downloaded to the mobile device 130 from a network-connected device such as the server 150 via the network 140.

The memory storage device 354 includes a machine-readable medium on which is stored one or more sets of instructions (e.g., software) embodying any one or more of the methodologies or functions described herein. The instructions may also reside, completely or at least partially, within the memory storage device 354, the ROM 350, the RAM 352, and/or within the processors 310 or 316 during execution thereof by the mobile device 130. The instructions may further be transmitted or received over a network, such as the network 140 in FIG. 1 via the network transmitter receiver 330. While the machine-readable medium is shown in this example to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media.

A variety of different types of memory storage devices, such as a random access memory (RAM) or a read only memory (ROM) in the system or a floppy disk, hard disk, CD ROM, DVD ROM, flash, or other computer readable medium that is read from and/or written to by a magnetic, optical, or other reading and/or writing system that is coupled to the processor, may be used for the memory or memories in the user device 130.

The data-management software running on the mobile device 130 may be a collection of programs or computer code that receives and processes measured data and/or other input. The data-management software processes and/or displays this input in a manner that is desired or selected by the user or other individuals. This information may be used by a user, home care provider (HCP), a physician, and/or other individuals. As discussed previously, the measured data may include information from the testing of an analyte including the concentration of glucose and/or other analytes in a person's blood or other fluid. The software can provide the advanced displays and data processing that may be required by a user who tests multiple times a day (e.g., from about six to about ten times a day). For example, the software may include a product similar to WINGLUCOFACTS® Diabetes Management Software available from Bayer HealthCare LLC (Whippany, New Jersey). As such, the software may provide a complete tool kit that receives and stores test results from a blood glucose-measurement system, receives and stores other testing information, such as test times and meal markers, tracks test results in an electronic logbook, calculates averages and provides other statistical analysis, summarizes and provides feedback on the test results, provides a customizable graphical user interface, displays user-friendly charts and graphs of the test results, tracks test results against user-specific target ranges, provides predictive analysis, and/or sends data to healthcare providers via fax, email, or the like.

The system 100 is not limited to receiving and managing information from the testing of an analyte, such as blood glucose. Indeed, the system 100 may receive data from other systems or devices that measure and/or record health data and do not require analyte testing, such as body-temperature measurements, blood-pressure measurements, heart rate measurements, blood-oxygen content measurements, breathing measurements for chronic obstructive pulmonary disease (COPD) analysis, weight measurements for analyzing Lasix use, or the like.

In addition, the software may employ data storage, such as an embedded database, for receiving and storing test results. The system 100 addresses issues related to the security of data, such as personal medical information, by ensuring: (1) essentially all data is stored and processed on the mobile device 130, which remains in the user's possession; and (2) no readable data is permanently transferred from the data storage to the server 150, which other individuals may access. Thus, a user may use a public computer to interface with the system 100 and no data remains on the public computer for others to view. Although the system 100 may temporarily transfer data to RAM or other similar storage on network devices such as the computer 170, a cleanup or termination procedure in the system 100 ensures that any such transferred data is removed from the computer 170.

Data security may also be enhanced by employing the data storage (e.g., an embedded database) that can only be accessed or decrypted by the data-management software. Furthermore, the software may also include programs or components, such as user-authentication routines, that protect data integrity and security. When the data-management software launches, it may immediately prompt the user for a user ID and password, personal identification number (PIN), and/or other authentication information. The user is only allowed access to data on the mobile device 130 if the response to the security prompt corresponds with authentication information stored with the data-management system 100. A user-authentication routine may also be employed to permit data to be transferred from the mobile device 130 to the server 150.

Additionally or alternatively, the transceivers 258 and 334 in FIGS. 2B and 3 respectively also may enable the testing device 110 and the mobile device 130 to communicate via a radio-frequency (RF) link (e.g., a short-range RF telemetry), such as Bluetooth® wireless technologies, Zigbee, Z-Sense™ technology, FitSense, BodyLAN™ system, and other RF technologies. RF technologies such as Bluetooth® enable external devices to communicate wirelessly with, for example, laptop personal computers and mobile phones. Other wireless, or non-physical, communication technologies, such as infrared (IR) links, also may be used.

In addition to storing data, such as test results from a blood glucose-measurement system and other health data processed by the data-management software, the mobile device 130 may be employed to incorporate the function of a portable medical records device, due to its portability and compatibility. As such, the mobile device 130 may be used to facilitate the sharing of important information with emergency medical technicians (EMT's), doctors, other health care providers, or the like.

In a particular embodiment, the mobile device 130 may provide important information during emergency situations. If the user is unconscious or otherwise unable to communicate with a care giver, the care giver may connect the mobile device 130 with a computing device and once the data-management software is launched, important information may appear on a splash screen or initial screen. This type of functionality is possible, because the mobile device 130 is highly compatible with a variety of computing devices, and the care giver does not have to pre-install software components on such devices to launch the software.

In some cases, data-management system software or applications may be distributed to the health care community, so that data on the mobile device 130 may be accessed, if authorized, with the data-management system software installed on the health care provider's processing device such as the computer 170. For security purposes, data may be encrypted so that it may only be read with a decryption key on the health provider processing device.

In general, the types of data that can be stored and shared with other individuals, such as health care providers, include, but are not limited to: name and address information; data tracked for a disease state (logbook information, daily tracking for chronic illnesses and measurable markers, measurements collected over the last 12 hours, etc.); comorbidity data; last dose of insulin or other medication taken; primary doctor's name and contact information; information on past visits to a doctor; a living will; information on a health care proxy; insurance information; allergy information; and other user-provided information. Alternatively or additionally, information can be provided on a sticker or other label affixed to the mobile device 130.

To preserve the user's privacy, information shared through the mobile device 130 is strictly controlled by the user. As a further technique for controlling shared data, the data-management software may provide multiple levels of access so that certain types of data are only accessible to certain individuals/organizations. For example, an EMT may only be able to access information such as doctor's information and data generally available on a medical bracelet. In other words, the software provides very basic functionality, e.g., displaying a single splash screen, to present less sensitive personal information to those without higher authority. Meanwhile, a doctor may be able to access more sensitive health-related information. Furthermore, greater access may be provided to relatives or close care givers, e.g., parents of a child with diabetes.

As described previously, the mobile device 130 may include a variety of interfaces to connect and communicate with a variety of devices. The mobile device 130 may employ its communication capabilities to connect remotely, e.g., over a network, with external systems to provide the user with a wider range of functionalities and features. In some embodiments, these external systems may provide a host function that manages the communication between the mobile device 130 and these external systems. These external systems may execute aspects of the data-management software or other software components stored on the mobile device 130 to enable the communication between the mobile device 130 and the external systems. Alternatively, these external systems may store the necessary software components locally.

Accordingly, the mobile device 130 may access the Internet or a cellular network, to transmit data remotely to other individuals, e.g., health care providers. As such, a user does not have to connect the mobile device 130 directly with the other individual's processing devices to share data. The health data stored on a mobile device 130 is therefore easily shared with other individuals, including health care specialists who may be located in distant or remote locations. This feature may be particularly advantageous for users unable to a health care provider's facilities due to health problems, distance, cost, etc. Moreover, this feature enhances the health care provider's ability to monitor a user's health data with greater frequency and immediacy.

In addition, the mobile device 130 may connect to the network 140 to receive field upgrades to the data and/or software stored on the server 150. For example, the mobile device 130 may conveniently receive an updated/patched version, or even a completely new version, of the data-management software by connecting to a remote download server. As a further example, the mobile device 130 may receive new or updated parameters for the execution of software or applications on the mobile device 130. In some embodiments, new programs or features for the system 100 may be received, e.g., purchased, from a remote download server. Optional features that may customize or personalize the graphical user interface for the data-management application may be available through a system accessible through the Internet. To maintain the integrity of the data and software on the mobile device 130, data or software downloaded via field upgrade may be validated before being employed in the mobile device 130. For example, checksum routines may be employed to confirm that data or software has been successfully downloaded in its entirety. The mobile device 130 may include a processor that can locally execute software components to manage aspects of the field upgrade. For example, the processor on mobile device 130 may preserve data integrity on the mobile device 130 according to a data update file (DUF) or other component that ensures that the software has been successfully downloaded. For additional data security, the DUF be employed with data encryption/decryption.

The mobile device 130 may employ a USB interface to connect to a variety of devices. In conventional systems, standard USB is designed to provide connectivity between a processing device and peripheral devices, where the processing device acts as a host and the USB-enabled peripheral devices act as slaves. In general, with standard USB, only the USB host can initiate data transfers to the connected USB peripheral device, and the USB peripheral device can only respond to instructions given by the host. Thus, a USB-enabled peripheral device is not able to connect with other USB-enabled peripheral devices over a peer-to-peer communication channel.

Figure 4:
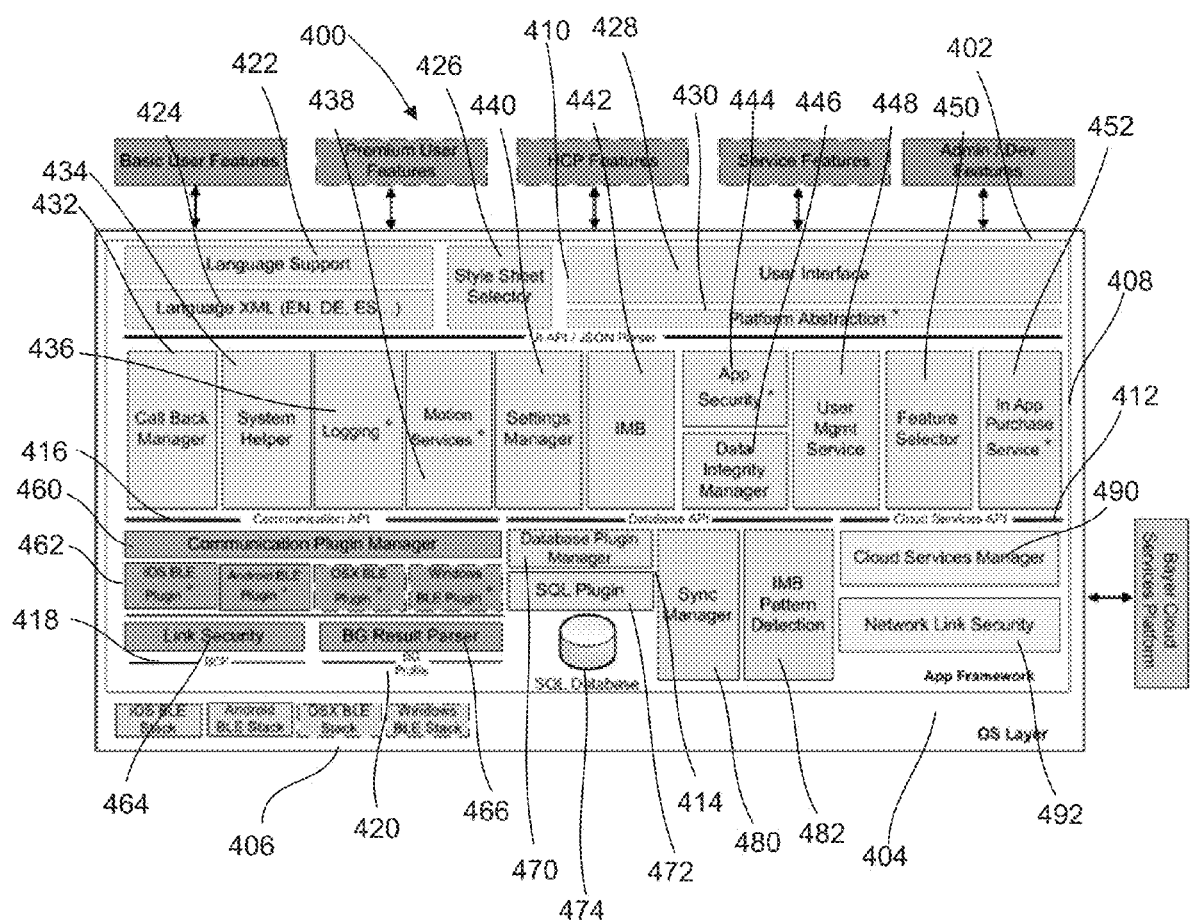
FIG. 4 illustrates a block diagram of the analyte data management and analysis application executed by the mobile device in FIG. 1.

FIG. 4 shows a block diagram of a management and analysis application 400 executed by the mobile device 130 in FIG. 1. As will be explained below, the management and analysis application 400 receives data relating to tests on fluids performed by the testing device 110 in FIG. 1 and provides management and analysis functions for a user. The management and analysis application 400 includes an application framework 402 and an operating system layer 404. The operating system layer 404 includes plug-ins 406 for different operating systems for different mobile devices such as Android, Windows, iOS and OSX.

The application framework 402 includes different APIs such as a user interface and JSON Parser API 410, a cloud services API 412, a database API 414, a communication API 416, a BCP API 418, and a blood glucose profile API 420. The application framework 402 includes middleware 408 that strings together the other functional modules and provides basic services to the application 400. While many of these services are platform-specific, they are small enough that they can be abstracted with simple methods.

The user interface API 402 includes a language support module 422, a language module 424, a style sheet selector 426, a user interface module 428 and a platform abstraction layer 430. The user interface 428 is written in HTML5 and encompasses dynamic HTML, JavaScript, and CSS style sheets. This dynamic HTML is manipulated by JavaScript within the pages as well as calls into and from the C/C++ middleware. The pages are packaged inside the application bundle. The platform abstraction layer 430 is a very thin piece of platform-specific shim code needed to instantiate and manage the mobile device's native browser engine, bind it to the application's main window, load the home page HTML from the app bundle, and handle the shuttling of code between the JavaScript and C/C++ worlds. In iOS/OSX, the browser engine is WebKit, in Android, the browser engine is Blink and in Windows, the browser engine is Internet Explorer.

The style sheet selector 426 manages the HTML's look and feel (e.g. to make the appearance more like native on a given platform), and potentially manage the selection of language-centric resources (e.g., specific language-translated text strings, styles, colors, left-to-right versus right-to-left, etc.). The platform abstraction layer 430 makes a decision about which specific CSS style sheets should be used by the HTML. The language support module 422 allows multi-language support. CSS style sheets are maintained for each supported language as described above, in order to allow language-specific formatting and layout, with text defined by a string ID. The language module 424 is an XML table of string IDs with each string translated into each supported language nested inside.

The middleware 408 includes a callback manager 432, a system helper 434, a logging module 436, a motion services module 438, a settings manager 440, an information, motivation, and behavior (IMB) manager 442, an application security module 444, a data integrity manager 446, a user management service 448, a feature selector module 450 and a purchase service module 452. The call back manager 432 is required by smart device operating systems, which operate by means of a callback mechanism. The application is not expected to run in the background or poll for the occurrence of certain events. Processing power and multitasking are limited on smart devices. Therefore, the host operating system provides a callback mechanism wherein an event trigger will call a callback function the application has provided to notify it of the event's occurrence. The callback manager 432 is the intended target of all these system callbacks and it calls the appropriate code elsewhere in the system when it receives them.

The system helper 434 notifies the application of system events and other information about the host operating system. For example, in iOS, this concept is known as a "delegate." The system helper 434 acts as the clearing house for these system notifications and services. Examples include posting system notifications, responding to time change events, etc.

The logging services module 436 provides centralized, unified access throughout the application to log functionality, such as displaying trace messages, general debugging information, and storing log files and reports.

The motion services module 438 handles sensors such as an accelerometer and a gyroscope in the mobile device 130. One intended purpose of these services is to handle a tap-to-pair bonding of the testing device 110 with mobile device 130, which requires knowledge of the device's accelerometer to detect a bump/tap, combined with analysis of the signal strength of the testing device 110 trying to pair to it.

The settings manager 440 manages the user's configuration settings, primarily for the application, but for aspects of configuration of the testing device 110 and cloud configuration as well. In this example, the settings manager 440 writes setting data to database 474, but it could also store in an XML, file, a .plist, a text file, etc.

The IMB manager 442 detects patterns in the user's data, and guides the user to recognize these patterns and alter his behavior to improve them, with the goal of helping the user manage his diabetes. The IMB manager 442 also detects information, motivation, and behavior pattern at appropriate times, and determine which information, motivation, and behavior patterns should be brought to the user's attention if many are detected. It is responsible for the long-term management of the user's experience.

The application security manager 444 acts as a bulkhead against hacking and tampering of the application. There are many potential vulnerabilities that may be mitigated or detected. Some of the identified vulnerabilities the application security manager 444 detects and mitigates include a jailbroken/rooted host device, a debugger attached, modified code, runtime code injection and swizzling of host OS routines.

The data integrity manager 446 ensures that the database 474 is encrypted, secure, and has not been tampered with. This includes normal data integrity (to make sure the database 474 has not been corrupted through normal accidental means, such as powering off the device, killing the application, battery loss, etc.) as well as tampering mitigation such as external editing or other compromise of the database 474. Example procedures include robust checksum calculation and monitoring, state checks, or database compacting.

The user management service 448 manages user identification and account management such as creating new users, remembering existing users, checking if passwords are correct, and allowing the user to manage his account. It makes use of cloud services manager 490 described below.

The feature selector module 450 validates the unlocking of features and manages their status with the rest of the application. For example, the application could be marketed as a "freemium" product, where the user receives basic functionality for free, but may optionally pay for premium features through the use of an in-application purchase described below. For example, the IMB and Bolus calculation may be locked out by a free installation but can be unlocked as premium features with an upgrade.

The in application purchase module 452 handles the invocation and management of the platform's native application store purchasing. The application purchase module 452 manages the instantiation of the native facilities and processes their results.

The communications API 416 includes a communication plug-in manager 460 and communication plug-ins 462, which in this example handle communications for the Bluetooth protocol for different operating systems. The communications manager 460 handles all forms of data communication with the application with the exception of cloud services support. As explained above, the example method of device communication is Bluetooth 4.0 (Bluetooth Low Energy, or BLE). It is contemplated that other methods of device communication may be used. Different plug-ins 462 may be accessed for different operating systems.

In this example, the plug-ins 462 include an iOS Bluetooth plug-in, an Android Bluetooth plug-in, an OSX Bluetooth plug-in and a Windows Bluetooth plug-in, but other plug-ins for other operating systems may be used. For example, the iOS Bluetooth plug-in wraps the functionality of iOS's CoreBluetooth stack into a neat, abstracted package behind the generic plug-in interface. The details of CoreBluetooth are not discussed here, but the high level functionality of the plug-in is to perform the following functions: initialize CoreBluetooth, check that BLE radio is turned on in control panel, scan for devices, present devices to the middleware as they are detected, connect to a device when the middleware asks, discover services and characteristics attached to a connected device, subscribe to characteristics and notify the middleware when an event happens, write to a characteristic when the middleware requests, disconnect from a device and handle unexpected disconnections.

Another example is the Android Bluetooth plug-in where the Android Bluetooth stack performs the same functionality outlined above for iOS, but the two stacks are completely different. The Android BLE stack, which was introduced in Android 4.3, is not discussed here. The Android plug-in wraps the functionality of the Android BLE stack behind the same interface used for the iOS BLE plugin.

The BCP API 418 includes a link security module 464 that provides additional security above and beyond what the BLE (Bluetooth) specification already provides. The link security module 464 may encrypt additional data over proprietary parts of the Bluetooth interface of the application so that only specific test devices or applications may decrypt/decode such data. Methods include shared secrets as a key for a hash algorithm, or the exchange of private keys. Another potential use of the link security module 464 is to provide access control, such that only authorized exchanges can access certain proprietary features.

The blood glucose profile 420 includes a blood glucose result parser 466. Regardless of what host operating system is doing the work, blood glucose results come as the result of notifications on a certain characteristic of the testing device 110 in FIG. 1. These notifications are packed and need to be decoded into human readable results. The blood glucose result parser 466 therefore may be shared between every platform; however, it is tightly coupled to Bluetooth so it does not belong elsewhere in the middleware. It can be a single piece of C/C++ code replicated in each plug-in.

The database API 414 includes a database manager 470 to handle the persistent local storage of data in the application, a sync manager 480, and a pattern detection module 482. In this example, the database manager 470 interfaces with an SQL plug-in 472 that interfaces with a database 474. The database 474 stores relevant data and settings required by the application 400. The database manager 470 interfaces with SQL plug-in 472, which wraps the functionality of the SQLite database into a generic plug-in interface. It is contemplated other types of databases may be used including a non-SQL database, an XML file, a prefs file, etc.

The sync manager 480 handles cloud synchronization of local database content up to the internet 140 in FIG. 1 and synchronizing the data returned from the internet 140. Ideally the sync manager 480 should be controlled by the cloud services manager 490. In this example, the sync manager 480 is very tightly coupled with SQLite, so it is located in the database API 414.

The pattern detection module 482 detects patterns in the user's data. For this reason, it is very tightly coupled with the database 474 instead of residing elsewhere in the middleware. The pattern detection module 482 looks for a set of patterns in the user's blood glucose readings and passes the results to the IMB module 442 in the middleware 408. As will be explained, pattern detection can be triggered on demand (e.g. after receiving a reading, determine whether it triggers a pattern) or in batch/offline/background mode.

The cloud services API 412 includes a cloud services manager 490 and a network link security module 492. The cloud services manager 490 acts as a centralized clearing house for all network-related services including any web technologies in general such as TCP/IP, UDP, sockets, HTTPS, SSL, etc. In this example, the cloud services manager 490 acts as a central hub for all cloud, internet, and third party connectivity. The cloud services manager 490 may provide WiFi/3G network detection, blood glucose reading synchronization, user account sync, settings, management, meter registration, online services, purchasing infrastructure and on line portals.

Figure 5A:
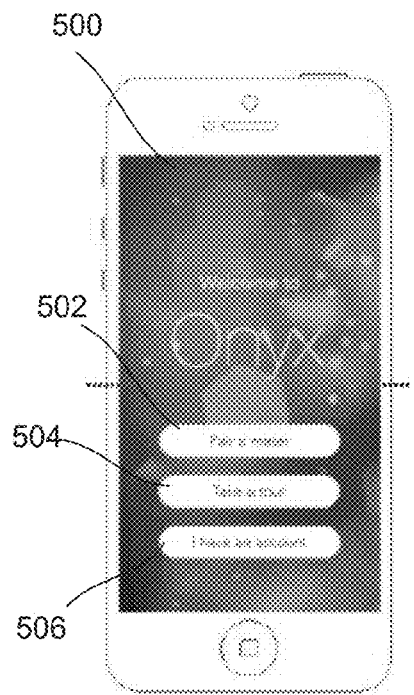
FIG. 5A illustrates an initial introductory interface screen for the data management application that may be displayed on the mobile device in FIG. 1.

FIG. 5A illustrates an introductory screen display 500 generated on a computing device such as the mobile device 130 in FIG. 1 by the data analysis and management application 400 in FIG. 4. The user may access the application with normal security measures for operating the mobile device 130 or alternatively with heightened security procedures as described above. The screen display 500 may also be generated by applications on other devices that communicate with the server 150. The introductory screen display 500 includes a pairing button 502, a take a tour button 504 and an account button 506. The pairing button 502 allows the user to access a screen to pair a testing device with the mobile device 130. In this example, multiple testing devices may be paired with the portable device if the user maintains an account on the server 150 in FIG. 1. In this example, if the user does not have an account, the user can only pair one meter with the mobile device 130. Other types of testing or metering devices such as health monitors, step trackers, personal fitness monitors, etc., may be paired with the mobile device 130.

The take a tour button 504 allows a user to be presented with an interactive training of data display and analysis functions on the mobile device 130 and guides the user through set up of a testing device paired with the mobile device 130 such as the testing device 110 in FIG. 2A via the application on the portable device 130. The take a tour button 504 may activate different sounds, display graphics or colors in the process of training a user in the functions of the application or the operation of the testing device 110. The account button 506, when selected, allows a user to access data related to the user stored on the database 160 in FIG. 1. The access includes secure identification of the user to access medical data. The account button 506 allows a user to create an account on the server 150. The account button also allows a user to register a meter or testing device with the account associated with the user maintained by the server 150 in FIG. 1. The user account managed by the server 150 as will be explained allows registration of meters and association of meters with the user as well as storage of data relating to the user.

Figure 5B:
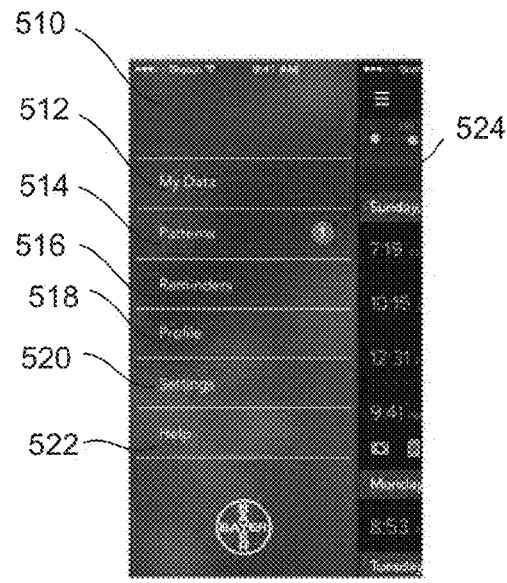
FIG. 5B illustrates a pull down menu-interface screen for activating different features that may be displayed on the mobile device in FIG. 1.

FIG. 5B shows a pull down menu 510 that allows a user to access the functions of the analysis and management program on the portable device 130. The pull down menu 510 is accessed in this embodiment from any screen by the user swiping a finger across the display of the mobile device 130. The pull down menu 510 includes a "My Data" selection 512, a patterns selection 514, a reminders selection 516, a profile selection 518, a settings selection 520 and a help selection 522. The "My Data" selection 512 will display data related to a current reading and additional information such as past readings as will be explained below. The patterns selection 514 will allow a user to detect any patterns in activity based on past reading data. In this example, the patterns selection includes a warning icon 524 that may indicate a pattern that that has been detected but which has not been read by the user.

The reminders selection 516 allows a user to display and control reminders that may be activated for different events. The profile selection 518 allows a user to display their medical profile that is used for testing. In this example, the profile is set for the user, although a primary health care provider or the user may change the profile to update information on the user's current medical condition. A setting selection 520 allows a user to set settings in relation to testing devices and their account on the server 150 in FIG. 1. A help selection 522 opens various help windows to assist the user in operating the application on the mobile device 130.

Figure 5C:
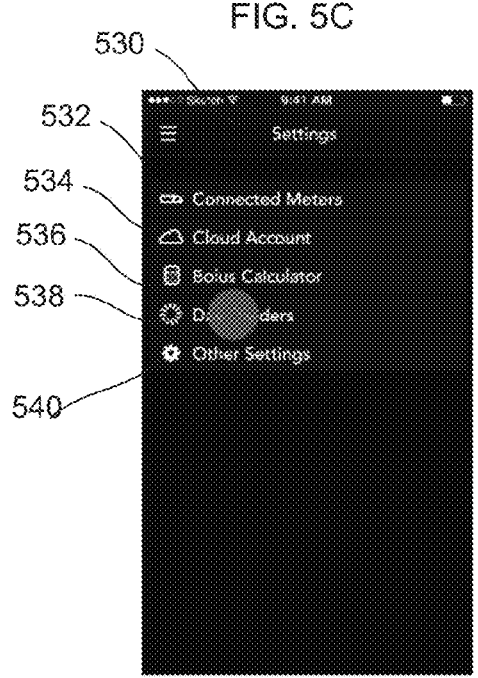
FIG. 5C illustrates an interface screen for controlling settings that may be displayed on the mobile device in FIG. 1.

FIG. 5C shows a setting screen 530 that is accessed by selecting the settings option 520 in the pull down menu 510 in FIG. 5B. The setting screen 530 includes a meters field 532, a cloud account information field 534, a bolus calculator field 536, a day dividers field 538 and "An Other" settings field 540. Each of the fields 432, 534, 536, 538 and 540 may be selected to expand and display additional selections to configure various functions in the application.

Figure 5D:
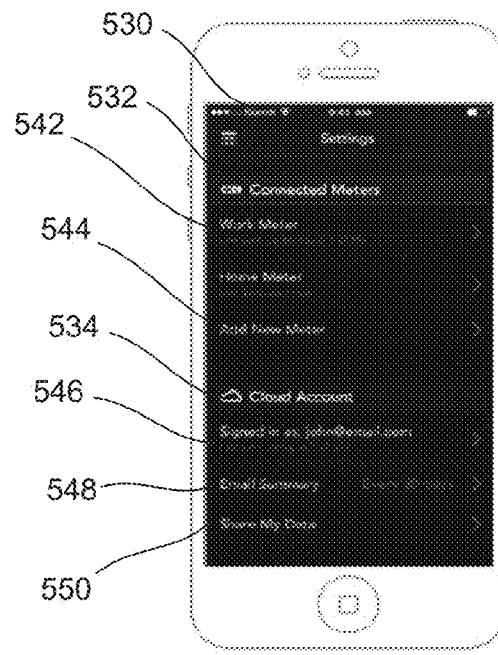
FIG. 5D illustrates an interface screen for configuring connected meters and a user account from the settings screen in FIG. 5C.

FIG. 5D shows the setting selection screen 530 where the meters field 532 and the cloud account information field 534 has been expanded. The meters field 532 now includes a listing of meters 542 that are in or have been in communication with the mobile device 130. The process of communication is pairing the mobile device 130 with a testing device such as the testing device 110 in FIG. 1. Each of the listings 542 includes the name of the meter and the last time the meter communicated with the mobile device 130 to transmit test data. The meters field 532 also includes an add meter button 544 which, when selected, allows a user to pair a new testing device or meter with the mobile device 130. In this example, the application on the mobile device 130 may pair up to four meters if the user has an account with the central server 150. If more than four meters are attempted to be paired, the meter with the longest interval from communication with the mobile device 130 is dropped.

The pairing procedure is initiated by selecting the add meter button 544. The mobile device 130 will display instructions to the user to pair a new testing device or meter. In this example, the testing device 110 is placed in proximity to the mobile device 130 and turned on. The push button 228 is depressed for a period of time until the illumination panel 232 turns blue indicating that a Bluetooth communication has been established. The user may then select information relating to meter such as the serial number to identify the meter with the mobile device 130. After required information is entered, the display on the mobile device 130 will then indicate a successful pairing and the new meter will be added to the meter field 532. In the case of a meter or testing device that has previously been paired, the display on the mobile device 130 will indicate a successful pairing has occurred. If the pairing is unsuccessful, the mobile device 130 will display information informing the user that the pairing was unsuccessful and display information for solutions to the problem. Any paired testing device may be unpaired by a user making an appropriate selection.

Once the mobile device 130 is paired with a meter or testing device such as the testing device 110, the mobile device 130 may display information obtained by the testing device in the same or greater detail. For example, the mobile device 130 may display information shown on the display 222 in FIG. 2C. The mobile device 130 may be used to configure different functions of the testing device 110 such as activating the illumination panel 232, activating the audio, test notification or setting target ranges. The mobile device 130 may also show errors in testing device operation and include information on how to correct the error.

The cloud account field 534 includes information and selection that allow a user to access their account on the database 160 via the server 150 in FIG. 1. The cloud account field 534 includes a sign on information field 546 that has information relating to the user and the last sign in on the account on the server 160. The user may select the sign on information field 546 to manage the account. An email summary information field 548 displays when results are emailed to the user and allows a user to set the frequency results are emailed. The results may be emailed in different formats or documents such as in pdf format. A "Share My Data" option 550 allows a user to share data related to the account to a third party such as a health care professional. Selecting the share "My Data Option" 550 will pop up a window with specific entry fields for the user to enter information relating to the third party to share the data. The account allows a user to backup and restore data to the application from the database 160 or other cloud storage.

Figure 5E:
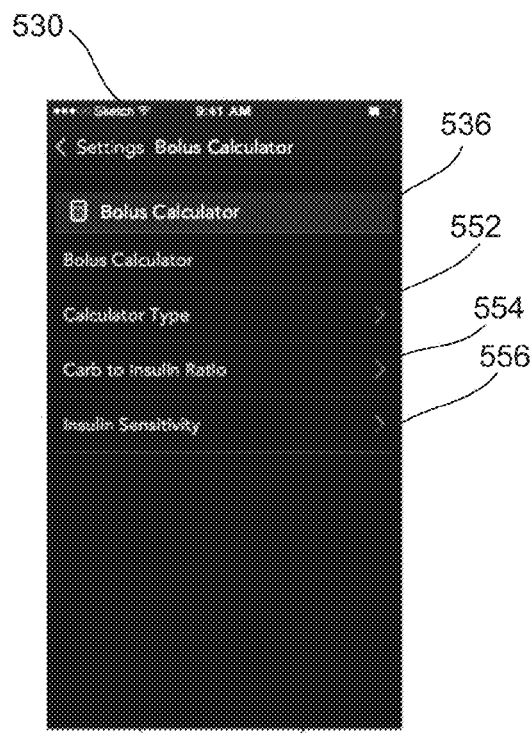
FIG. 5E illustrates an interface screen for configuring a Bolus calculator from the settings screen in FIG. 5C.

FIG. 5E shows the settings selection screen 530 where the bolus calculator field 536 has been expanded. A user may configure the Bolus calculator function by selecting between a calculator type field 552 which allows configuration of the calculator type, a carb to insulin ratio field 554 and an insulin sensitivity field 556.

Figure 5F:
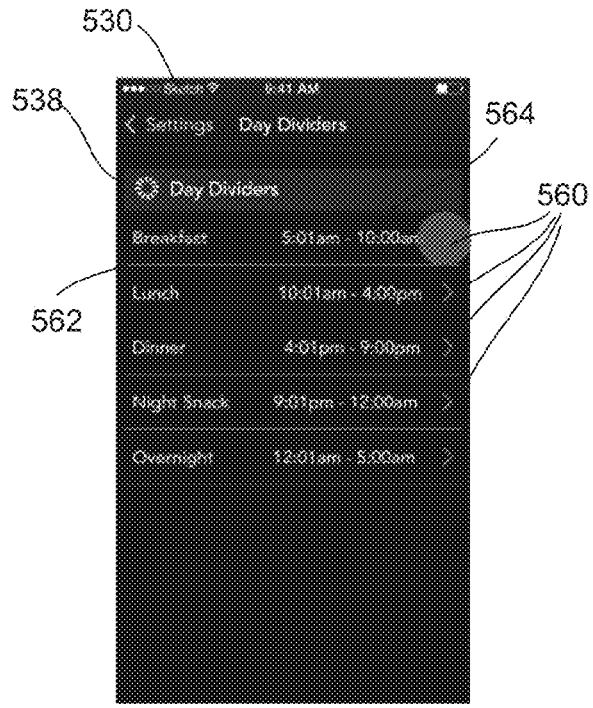
FIG. 5F illustrates an interface screen for configuring day dividers from the settings screen in FIG. 5C.

FIG. 5F shows the settings selection screen 530 where the day dividers field 538 has been expanded. The day dividers field 538 includes a listing of time divisions 560, which show the times of the day assigned to different divisions. For example, the configuration in FIG. 5F has five day dividers. Each of the listings 560 includes a description of the division 562 such as breakfast or lunch and a time range 564 associated with the division. A user may change the settings of the day dividers through pop-up windows that allow adjustment of times for each division.

Figure 5G:
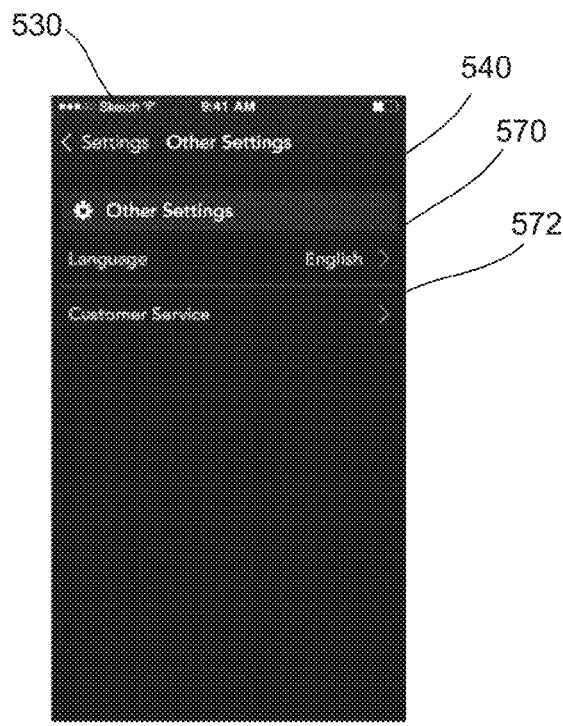
FIG. 5G illustrates an interface screen for configuring other settings from the settings screen in FIG. 5C.

FIG. 5G shows the settings selection screen 530 where the other settings field 540 has been expanded. The other settings field 540 includes a language selection field 570 that allows a user to choose the language of the application and a customer service field 572 that allows a user to contact customer service.

Figure 5H:
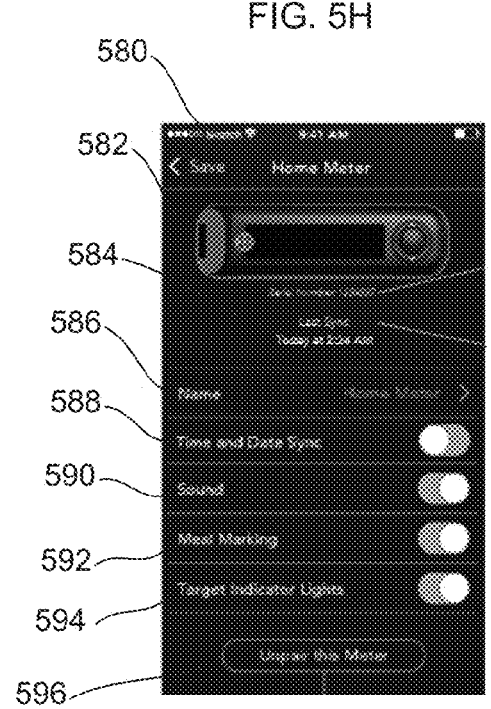
FIG. 5H illustrates a meter information screen that allows a user to configure a meter in communication with the mobile device in FIG. 1.

FIG. 5H shows a meter information screen 580 that is displayed when any of the meters in the meter listing 542 in FIG. 5A are selected. The meter information screen 580 includes a graphic of the meter or testing device 582, a last sync time 584 and a name field 586. The user may configure the meter or testing device by selecting a time and date sync toggle switch 588, a sound toggle switch 590, a meal marking switch 592 and a target indicator light toggle switch 594. The meter or testing device may be unpaired by selecting an unpair button 596.

The graphic of the meter or testing device 582 includes the serial number of the meter of the testing device for identification purposes. The name field 586 may be selected by the user to enter the name of meter or testing device to distinguish it from other testing devices paired with mobile device 130. The last sync time 584 will display the date and time the last time data from the testing device was synchronized with data on the mobile device 130.

Figure 6A:
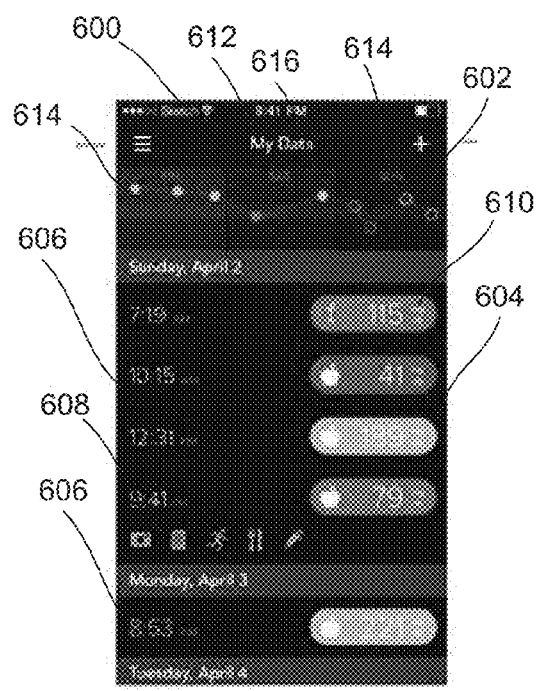
FIG. 6A illustrates a data display interface screen for displaying health readings on the mobile device in FIG. 1.

FIG. 6A shows a personal data screen 600 that is displayed when the "My Data" selection 512 is selected from the menu 510 in FIG. 5B. In this example, the personal data screen 600 is the default screen displayed by the application. The personal data screen 600 includes a timeline area 602 and a reading display area 604. The reading display area 604 includes a series of date windows 606 that represent readings for a particular day. In this example, the readings are arranged in chronological order, although the readings may be displayed in any order. In this example, a user may scroll down to show the most recent readings near the bottom of the screen 600. The date window 606 includes a series of marker icons 608 that may be selected for a particular day to include different occurrences with a particular reading. For example, the marker icons 608 may include a photo icon indicating an associated picture, a notes icon indicating an associated note, an exercise icon indicating the reading occurred after exercise, a meal icon indicating the reading occurred after a meal, or an insulin icon that indicates a dosage of medication.

The date windows 606 include listings 610 for each reading taken by the user and the resulting measured blood glucose data. The listing 610 includes the time the reading was taken, the reading value and a log icon which in this example may be pre-meal, post meal or no meal. The reading value may be framed in a green color indicating the reading value is within an associated target range, red indicating the reading was below the target range or orange indicating the reading was above the target range. It is contemplated that other colors, patterns or visual indicators may be used to indicate the reading value relative to the target range.

The timeline area 602 includes a graph 612 that plots the readings over a period of time (e.g., three days in this example). A longer or shorter time period for plotting the readings may be used. The graph 612 includes circles 614 that represent the time of day readings occurred based on measurements taken from the test device 110 and communicated to the mobile device 130. The circles 614 may be colored according to the readings in relation to the target range. An outline of the dots is displayed for the day that is at the top of the screen in the date window 606. In this example, the four readings in the listings 610 for Sunday are displayed as outlines in the graph 612. A plot line 616 shows the different values of the circles 614 relative to a blood glucose scale. In this example a different shape such as a diamond may be plotted for manual entries by a user of readings in situations where the data is not automatically received by the mobile device 130.

Figure 6B:
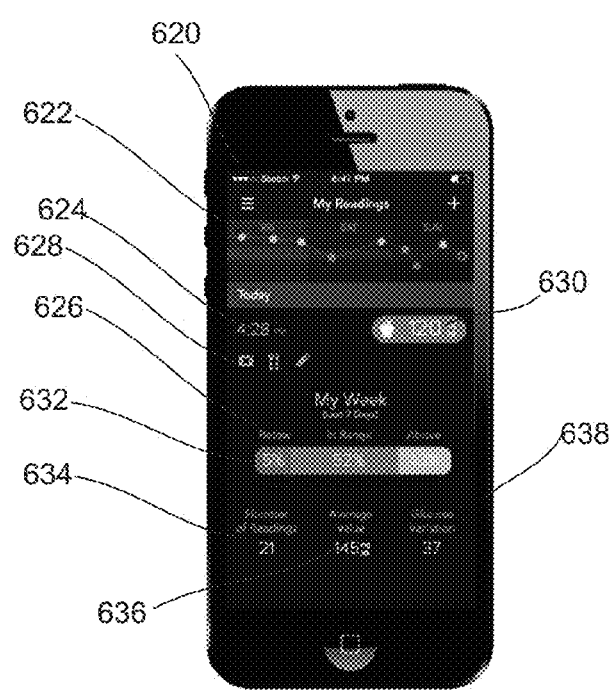
FIG. 6B illustrates a summary average data display interface screen for displaying health readings on the mobile device in FIG. 1

FIG. 6B shows an averaging data display screen 620 that may be displayed on the mobile device 130. The display screen 620 is displayed by the user collapsing the listings 610 in FIG. 6A into a smaller current reading area 624 in FIG. 6B. The display screen 620 includes a timeline area 622 that is identical to the timeline area 602 of the data listing screen 600 in FIG. 6A. The display screen 620 also has a current reading area 624 and a weekly reading area 626. The current reading area 624 includes a series of icons 628 that indicate markers the user has associated with the reading. The current reading area 624 also includes the reading in a field 630 that is in a color signifying whether the reading is within the targeted range or above or below the targeted range. The reading field 630 also includes an icon indicating a pre-meal or post-meal reading.

The weekly reading area 626 includes an information bar 632. The information bar 632 categorizes readings from the week in three different color areas indicating how many readings were within range (green middle), above the range (orange left) and below the range (red right). The length of each color area corresponds with the number of readings falling in the ranges represented by the area in the information bar 632. The information bar 632 also indicates percentages of readings in each of the three areas as well as the number of readings in each area. The weekly reading area 626 also includes a number of readings field 634, an average reading value field 636 and a variation field 638 that all provide summary data on the readings during the period the averages are computed.

In this example, the screen 600 in FIG. 6A or the screen 620 in FIG. 6B is displayed when the user orients the mobile device 130 in a portrait direction. If the user turns the mobile device 130 to display in landscape, the display is changed to a detailed data screen 640 shown in FIG. 6C. The detailed data screen 640 includes an expanded graph 642. In this example, the vertical axis of the graph 642 represents the value of blood glucose while the horizontal axis is a time scale. The expanded graph 642 in this example shows one day of readings, although longer or shorter time periods may be displayed. The expanded graph 642 includes plot points 644 that are in a circular shape. Each of the plot points 644 represents a reading and shows the value of the reading within the circular shape. As with the previous graph in FIG. 6A, the circular shape of the plot points 644 may be colored to indicate the reading is within range or above or below range. As with the previous graph in FIG. 6A, a different shape such as a diamond may be used to represent a manual entry by the user. A plot line 646 connects the plot points 644.

The graph 642 also includes different icons indicating other entries in the associated user log book. For example, a series of note icons 648 indicates that a user entered notes when a reading was recorded. A larger note icon 652 indicated the entry of a note that was not associated with a reading. The note icon 652 appears on the plot line 646 at the time the note was entered. A camera icon 650 indicates a picture was taken with the camera 322 on the device 130. The readings of another day may be displayed by a slider control 654, which may be moved to select other dates. Alternatively, the user may swipe the screen right or left and move the graph to display days before or after the day displayed. The data from a default day displayed is the current day, but another default time period may be used. An insulation bar 656 indicates the number of units of insulin taken as well as the times.

Figure 6C:
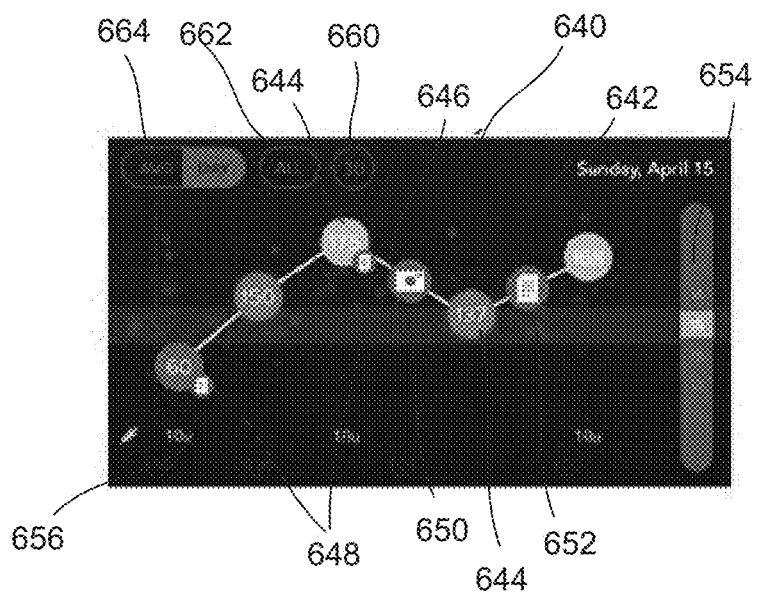
FIG. 6C illustrates a data display interface screen for displaying health readings on the mobile device in FIG. 1 when turned in landscape orientation.

A date range selector 660 allows a user to filter the data on the graph 642 by a selected number of days. In FIG. 6C, the user has selected data from 30 days as shown in the selector 660, but other selections such as 3, 7, 14 or 90 days may be selected. A meal marker selector 662 will display a drop down menu that allows a user to select between different meal markers. Thus, when all is selected in the meal marker selector 662 of FIG. 6C, all data is shown. If a pre-meal marker is selected for the meal marker selector 662, data only for before meal readings is displayed or if an after meal marker is selected, data only for after meals is displayed. The appropriate associated icon is shown in the meal marker selector 662 to indicate which marker filter is currently being used.

Figure 6D:
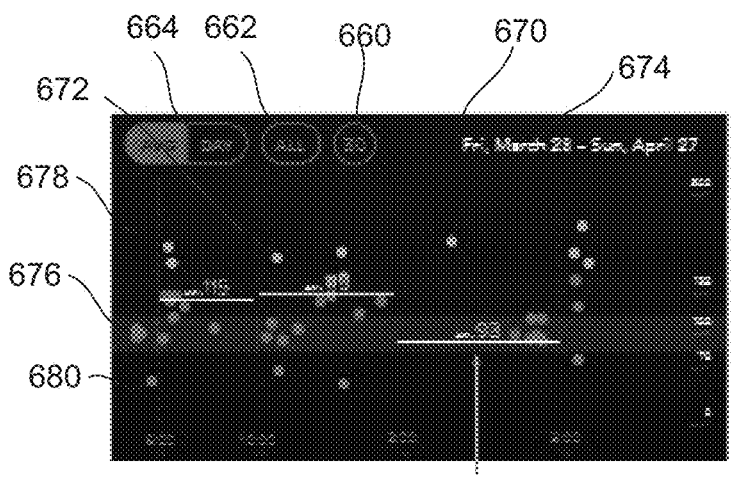
FIG. 6D illustrates another data display interface screen for displaying health readings on the mobile device in FIG. 1 when turned in landscape orientation.

The display data may be changed via a day/average switch button 664. In this example, day has been selected and thus the display in FIG. 6C shows daily readings. By toggling the button 664 to select average, the average data display 670 in FIG. 6D is displayed. The display 670 shows plots over a period of time on a graph 672. A range of dates 674 for the data displayed on the graph 672 is shown near the top of the display 670. The graph 672 includes time of day, and various data points are plotted depending on the time of day they were taken during the period of time. Certain data points 676 falling within the target range and are indicated by a green color. Certain data points 678 exceeding the target range and are indicated by an orange color. Certain data points 680 falling under the target range and are indicated by a red color.

Figure 6E:
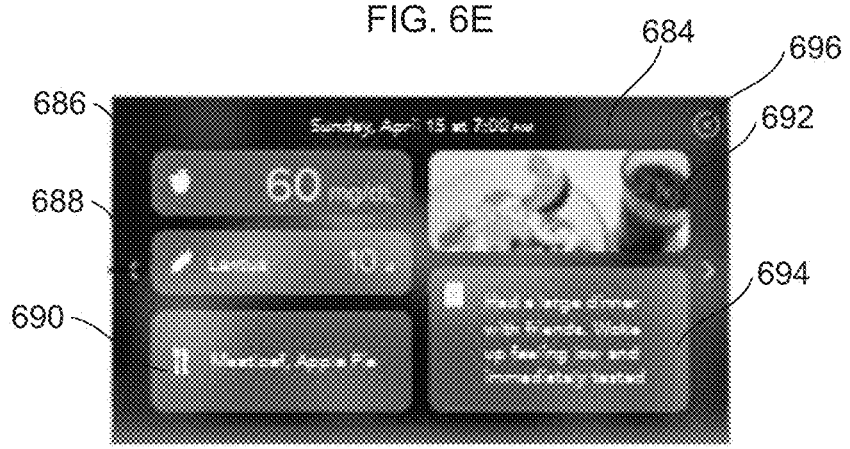
FIG. 6E illustrates a screen showing detailed information on a log entry on the mobile device in FIG. 1.

Detailed information for each reading may be accessed by selecting or touching a particular reading. FIG. 6E shows a detailed information screen 684 that may be displayed by selecting one of the plot points 644 in the display 640 in FIG. 6C or the readings in the display 600 in FIG. 6A or the display 620 in FIG. 6B. The selection may be made by tapping the area of the display or by another selection input on the mobile device 130. The detailed information screen 684 shows the date and time of the reading at the top of the screen and includes a reading field 686 showing reading selected. The reading field 686 may be colored coded to indicate whether the reading was within the target range or above or below the target range. An insulin area 688 shows whether insulin was taken and what amount was taken. A meal description area 690 displays information about the meal. A photo area 692 shows any associated pictures with the reading. A notes area 694 displays any notes entered by the user associated with the reading. The detailed information screen 684 may be closed by selecting a cancel icon 696.

Figure 7A:
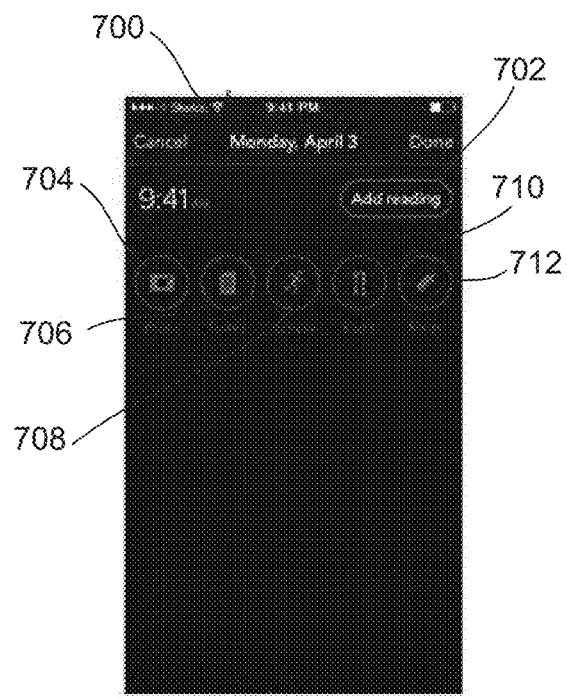
FIG. 7A illustrates a manual entry screen for entering data in a log book via the mobile device in FIG. 1.

FIG. 7A illustrates a manual entry screen 700 for adding a manual entry by the user of the mobile device 130. The manual entry screen 700 may be accessed from the list view of any screen shown by the application. The screen interface 700 includes an "Add Reading" button 702 that allows a user to manually enter a blood glucose value. The user may also add different entries through selecting a camera icon 704 for adding a picture, a notes icon 706 for adding notes, an activity icon 708 for adding the occurrence of an activity, a food icon 710 for entering food data, and a med icon 712 for entering medication data. Each of the icons 704, 706, 708, 710 and 712, if selected, opens additional screens to allow a user to load the corresponding entry.

The camera icon 704 opens a series of screens that allow a user to add a picture taken from the camera of the mobile device 130 or stored in any storage device accessible by the mobile device 130. The notes icon 706 opens a key board that allows a user to enter a note. The activity icon 708 opens screens to enter or select a description of the activity, the duration of the activity, and the intensity of the activity. The food icon 710 opens screens to allow a user to enter or select a description of the food, and nutritional information such as the calories of the food per serving. The med icon 712 opens screens to allow a user to enter a description of the medication and other information such as the dosage of the medication.

Figure 7B:
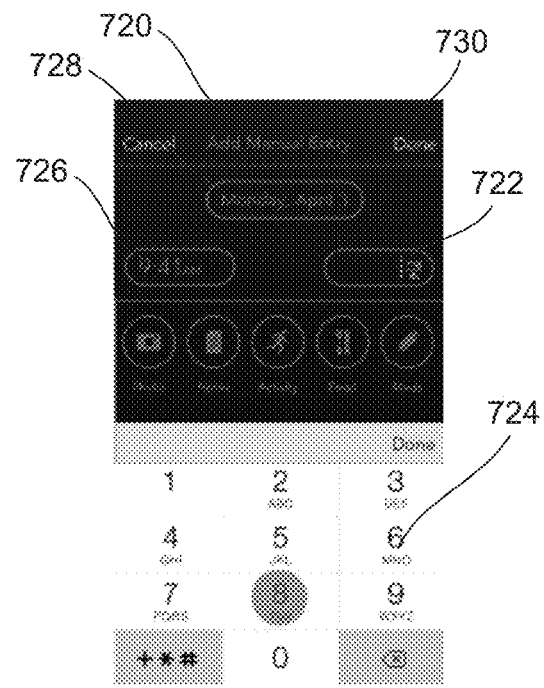
FIG. 7B illustrates a manual reading entry screen for entering a reading by the user of the mobile device in FIG. 1.

FIG. 7B shows a pop up screen 720 for entering data relating to a manual reading entry. The user may enter the concentration amount in a concentration reading field 722 via a displayed numerical key pad 724. The user may select the time via a time selection field 726 and the date via a date selection field 728. Once the user completes the entry of the concentration value, date and time, the user can select a done button 730 and the application will return to the manual entry screen 700.

Figure 7C:
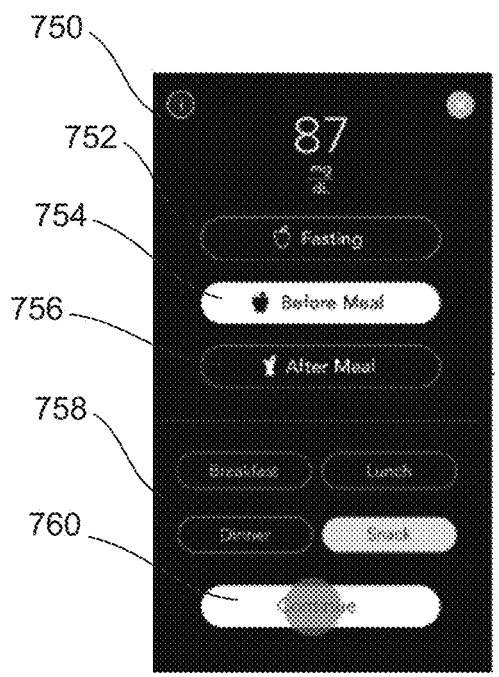
FIG. 7C illustrates a manual meal marker entry screen for entering a meal marker by the user of the mobile device in FIG. 1.

If the "Add Reading" button 702 is selected and data is entered via the pop up screen 720, an additional meal marker icon is displayed on the manual entry screen 700 to classify the reading. If the meal marker icon is selected, a meal marker entry screen 750 in FIG. 7C is displayed. The user can select between a fasting selection 752, a before meal selection 754 and an after meal selection 756. The user may also select between different meal buttons 758 to assign the reading to a particular meal. Once the marker is selected and the meal is selected, the user may exit the screen via a continue button 760. Once the manual entry is completed, it will show up as another entry in the data screens shown in FIGS. 6A-6D.

As explained above, the application will detect patterns based on the gathered data and inform the user of the pattern and suggest corrective action if necessary. Information on patterns may be displayed by selecting the patterns field 514 on the pull down menu screen 510 in FIG. 5B. Information on patterns may also appear when they are detected in the form of a pop up window.

Detected patterns may be of the active, additional, or archived categories. The patterns may further also have one of a dismissed status, an improved status or a timed out status. After opening a pattern, if a user dismisses the pattern, the pattern has a dismissed status. For each pattern, a set of criteria is assigned to improve. When a pattern meets the criteria, the pattern has an improved status and can be moved to the archived category. Each pattern has a predetermined time in which a time out status will be assigned. If nothing occurs, the pattern times out after the predetermined time and is moved to the archive category.

Patterns in the active category are determined by the priority level and group consideration. Active patterns include data meeting the pattern currently. A user may select patterns to move to active status. As will be explained below, a user will be informed of active patterns and read information on the pattern.

Patterns in the additional category are patterns that are not collecting data and are determined by priority level, group and date of detection. An active pattern may be altered to the additional category if the user improves the data that led to the pattern. The user is offered the option of obtaining information relating to the additional pattern or to dismiss the pattern. Any recognized pattern that has been dismissed or improved is moved to the archive category and stored.

Patterns may be indicative of actions that could be improved or those that could be beneficial practices. For example, patterns indicative of the need for improvement may include high or low readings after a specific meal, high or low readings before a specific meal, lack of consistent testing frequency, lack of consistent testing at set times of the day, low frequency of testing, high or low readings at a particular time of the day, approaching critical high or low readings consistently, and high or low days of week. Patterns that are beneficial may include a best time of day for balanced blood sugar or consistent testing.

Figure 8A:
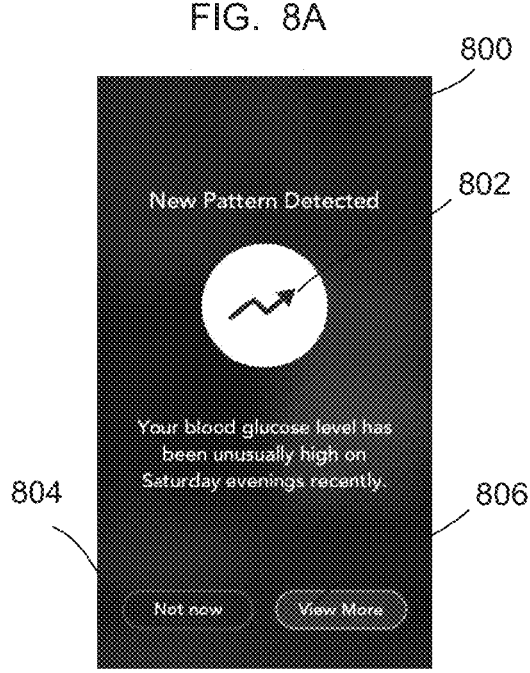
FIG. 8A illustrates a pattern notification screen to inform a user of a pattern on the mobile device in FIG. 1.

FIG. 8A is a pattern notification screen 800 that occurs to warn a user of patterns based on readings analyzed by the application on the mobile device 130. When a pattern is detected, an icon appears on the display of the mobile device 130 regardless of whether the application is currently active. The pattern notification screen 800 may be displayed by a user selecting the icon. The pattern notification screen 800 includes a graphic 802 indicating whether the pattern is beneficial or problematic. In this example, an arrow trending up or down indicates that the pattern is increasing. The pattern notification screen 800 also includes information relating to the detected pattern. In this example, a pattern has been detected that the user's blood glucose level has been unusually high for Saturday evenings. In contrast, a beneficial pattern may display a smiley face or other similar graphic. The pattern notification screen 800 includes a view more button 806 that allows a user to obtain more information about the discovered pattern. A not now button 804 allows a user to ignore the detected pattern.

Figure 8B:
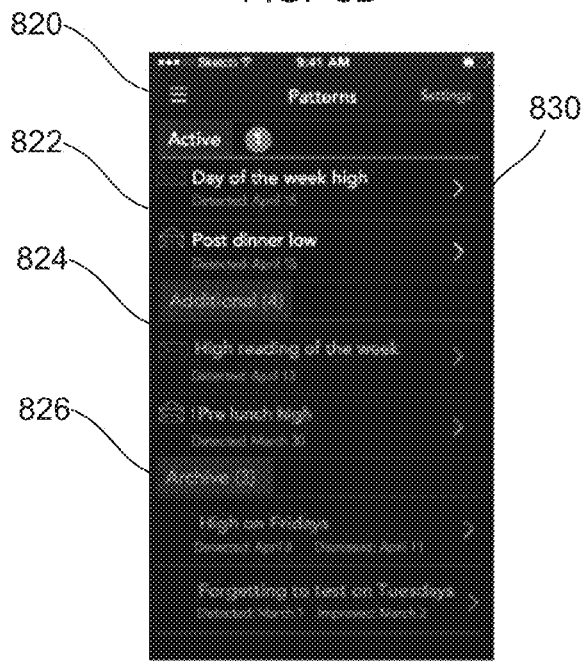
FIG. 8B illustrates a pattern management screen that shows current patterns on the mobile device in FIG. 1.

If the user selects the not now button 804, they will be returned to the pulldown menu 510 in FIG. 5B. The pattern selection 514 in the pull down menu 510 in FIG. 5B may have an icon indicating that one or more patterns have been unread by the user. Selecting the pattern selection 514 in the menu 510 will result in a pattern management screen 820 to be displayed as shown in FIG. 8B. The pattern management screen 820 includes an active tab 822 showing active category patterns, an additional category tab 824 showing additional patterns and an archive tab 826 showing archived category patterns. The tabs 822, 824 and 826 may be expanded as shown in FIG. 8B to show all patterns under each category. As shown in FIG. 8B, the active tab 822 shows an indicator of the number of patterns that are unread by the user. Each of the tabs 822, 824 and 826 lists all patterns under that category. Listed patterns will include a description of the pattern, the time the pattern was detected and whether the pattern was improved or dismissed.

Figure 8C:
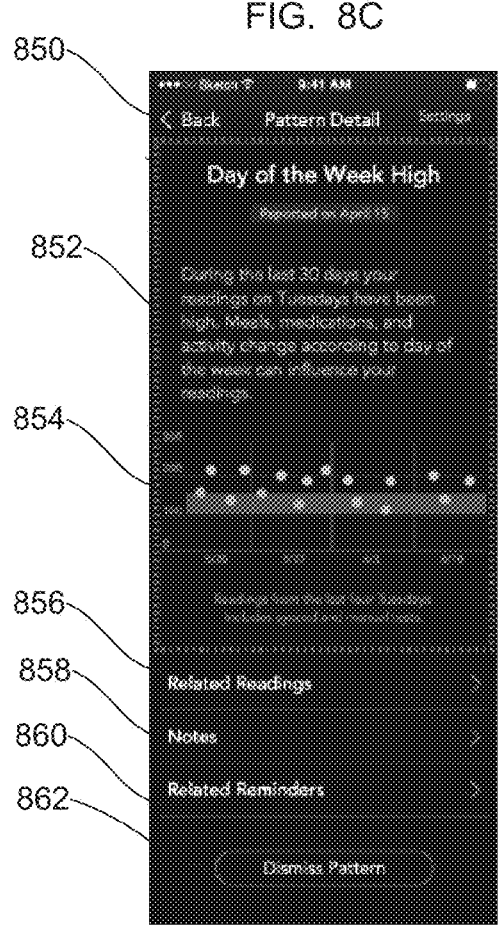
FIG. 8C illustrates a pattern detail screen to convey additional information on a pattern on the mobile device in FIG. 1.

A user may select the view more button 806 in FIG. 8A or any of the pattern listings 830 in FIG. 8B that will access a pattern detail screen that shows the data supporting the analyzed pattern. The content of the pattern detail screen is geared toward describing the pattern and recommending corrective action. Pattern detail screens may therefore be tailored to the particular pattern. One example of a pattern detail screen 850 is shown in FIG. 8C. The pattern detail screen 850 includes a description 852 of the detected pattern which includes information about the pattern and potential factors that caused the pattern. A graph 854 is displayed that shows the readings that led to the pattern. A related readings tab 856 allows a user to display additional information about the readings that support the pattern. Such a display will include the date and time of the readings and the reading values themselves. A notes tab 858 allows a user to enter notes relating to the pattern. A related reminders tab 860 allows a user to set reminders of actions to potentially address the causes of the pattern. A dismiss pattern button 862 allows a user to dismiss the pattern. Other types of pattern detail screens may document improvements that address the pattern, reminders that the pattern has not been addressed, selecting the level of feedback on a particular pattern and information on follow up actions.

Figure 9A:
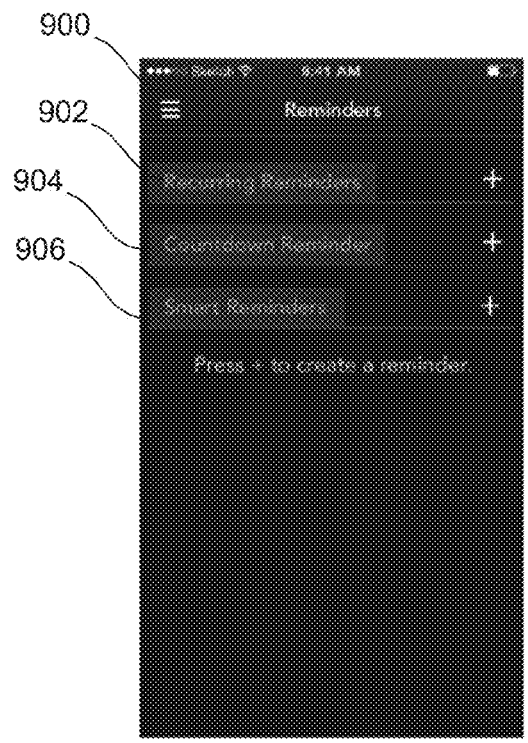
FIG. 9A illustrates a reminder setting screen to create a reminder on the mobile device in FIG. 1.

FIG. 9A is a reminder screen 900 that is displayed when a user selects the reminders option 516 in the pull down menu 510 in FIG. 5B. The reminder screen 900 includes a recurring reminders selection 902, a countdown reminder selection 904 and a smart reminder selection 906. Selecting any of the selections 902, 904 and 906 creates a reminder for the user.

Figure 9B:
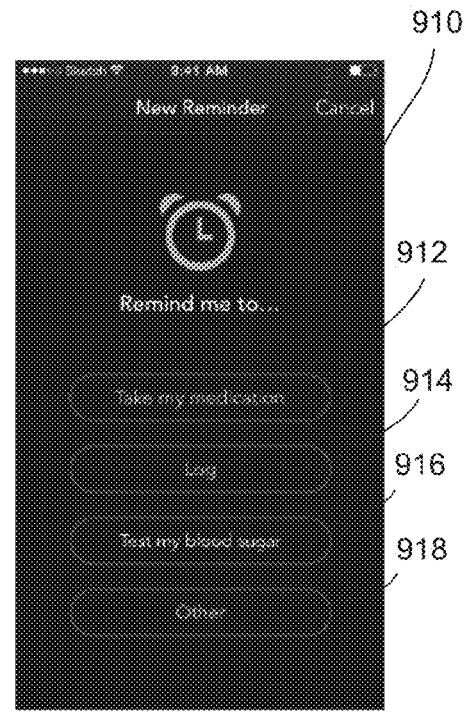
FIG. 9B illustrates a recurring reminder creation screen on the mobile device in FIG. 1.

The recurring reminder selection 902 creates a series of reminders based on a recurring reminder screen 910 shown in FIG. 9B. The recurring reminder screen 910 includes a "Take My Medication" selection 912, a log selection 914, a test my blood sugar selection 916 or an other selection 918.

If the user selects the test my blood sugar selection 916, an additional screen appears to allow a user to select between a specific time, after a pre-meal reading or based on location. Selecting a specific time allows the user to set a time and day to remind the user. Selecting after a pre-meal reading gives the user the option to set a time to remind the user to test their blood sugar if they haven't tested after a pre-meal reading. The selection of a time will start a countdown timer to the reminder. Selecting a reminder based on location allows a user to select a location for triggering the reminder.

If a user selects the "My Medication" selection 912, an additional screen is presented that allows a user to specify the medication and dosage. Another screen allows a user to select triggering the reminder for a specific time, based on blood sugar level or based on location. Other selection factors for reminders may be used. If the user selects the log selection 914, another selection screen is displayed to allow the user to select an item such as a photo, note, activity or food for entry into the log. Another screen allows a user to select the reminder for a specific time, based on blood sugar level or based on location.

Figure 9C:
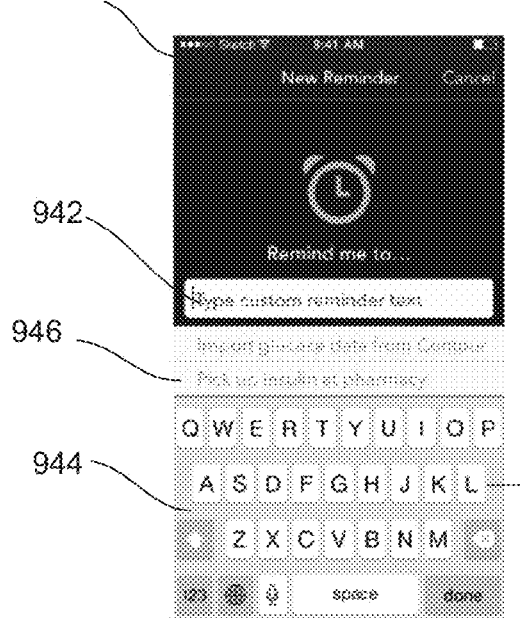
FIG. 9C illustrates an entry screen for creating a custom reminder on the mobile device in FIG. 1.

If the user selects the other selection 918, an entry screen 940 shown in FIG. 9C appears to allow a user to create their own reminder event. The entry screen 940 includes a custom reminder text field 942 that allows a user to enter a description from a keyboard 944 of the reminder. A listing of previous reminders 946 is also displayed allowing a user to select a previously entered reminder description. After entry of the description, another screen allows a user to select triggering the reminder for a specific time, based on blood sugar level or based on location.

Figure 9D:
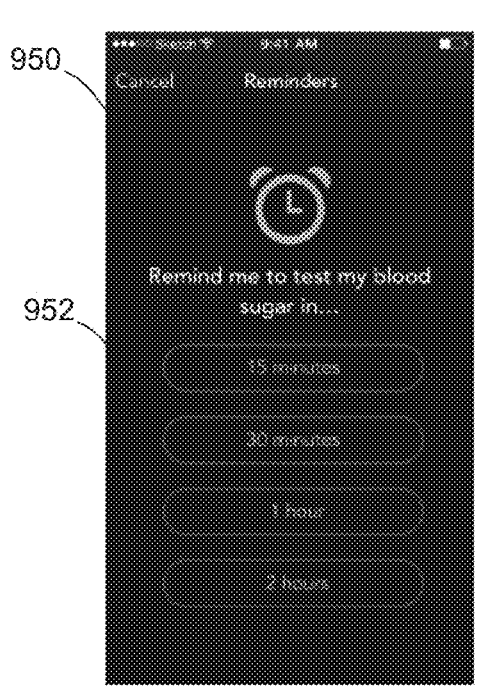
FIG. 9D illustrates an entry screen for selecting a time for a countdown reminder on the mobile device in FIG. 1.

FIG. 9D shows an entry screen 950 that is displayed if the countdown reminder selection 904 is selected in FIG. 9A. The entry screen 950 allows a user to set a time by selecting between time options 952. Once selected, the timer begins to countdown to the reminder time.

When the smart reminder selection 906 is selected in FIG. 9A, additional screens are displayed that include events such as visiting a health care professional that assist in managing the health of the user. The events are pre-set test reminders that may be used by the user to assist in managing health such as doctor visits, stressful events, and motivational messages. Each of these may be selected and additional information may be attached to the reminder. For example, the user may authorize sending medical data from the mobile device 130 or the data in a user account stored in the database 150 in FIG. 1 to a health care professional in advance of a visit as a part of that reminder.

Figure 10A:
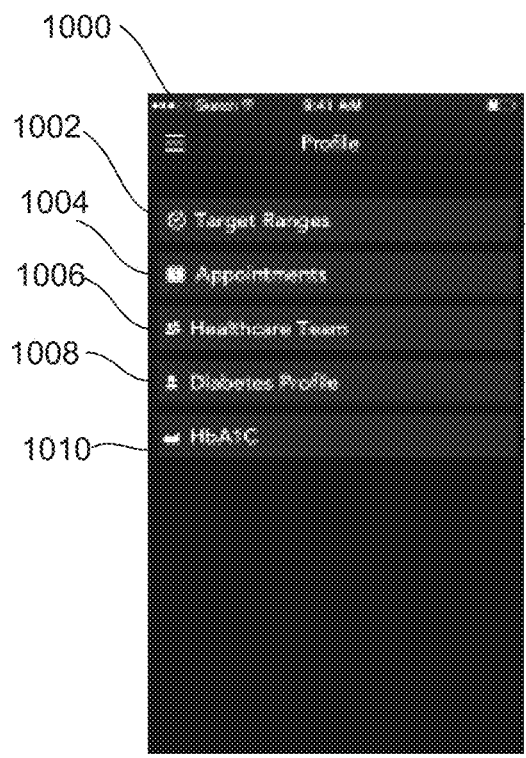
FIG. 10A illustrates a profile management screen for selecting a profile for configuration on the mobile device in FIG. 1.

FIG. 10A is a profile management screen 1000 that is displayed when the profile selection 518 is selected in the pull down menu 510 in FIG. 5B. The profile management screen 1000 includes a target ranges selection 1002, an appointments selection 1004, a health care team selection 1006, a diabetes profile selection 1008, and an HbA1c selection 1010. The appointments selection 1004 allows a user to configure information regarding appointments with health care professionals such as the date, time and location of such appointments. The user may also configure the mobile device 130 to send a report of relevant health data to the health care professional at a certain time before the appointment. The health care team selection 1006 allows a user to enter information relating to health care professionals such as contact information. The HbA1c selection 1010 allows a user to add new HbA1c values.

Figure 10B:
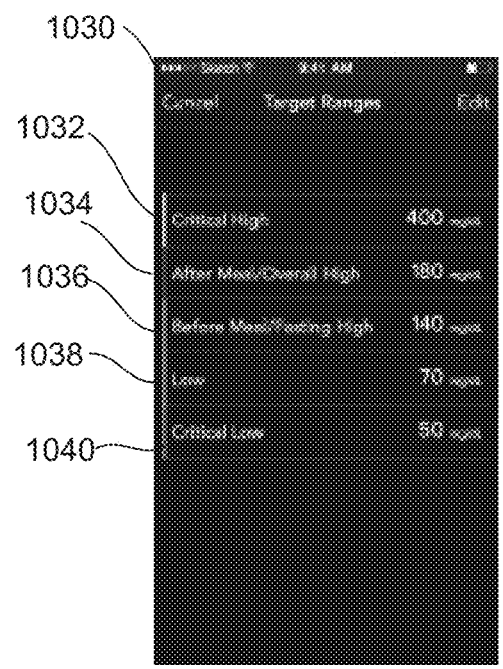
FIG. 10B illustrates a target range selection screen for selecting target ranges for the mobile device in FIG. 1.

Selecting the target ranges selection 1002 will display a range selection screen 1030 shown in FIG. 10B. The range selection screen 1030 includes a critical high field 1032, an after meal overall high field 1034, a before meal/fasting high field 1036, a low field 1038 and a critical low field 1040. The user may adjust the values for any of these fields which in turn determine various patterns and warnings as well as the color of readings that are displayed. In some cases, the user may agree that only a dedicated health care professional can adjust the target range values.

Figure 10C:
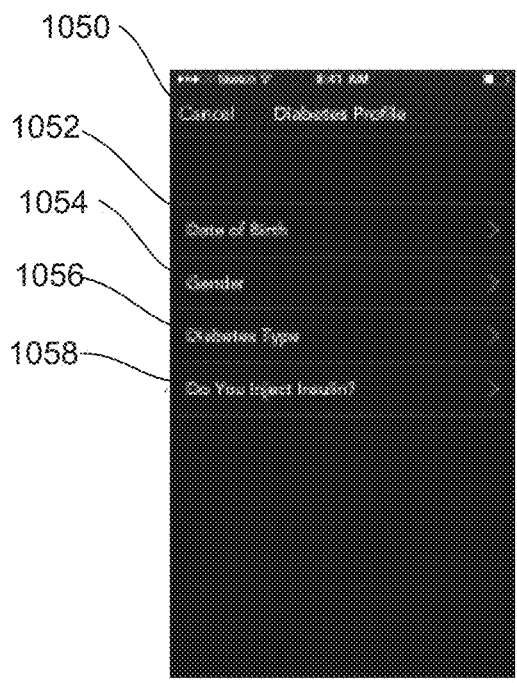
FIG. 10C illustrates a diabetes profile entry screen for the mobile device in FIG. 1.

FIG. 10C is a diabetes profile screen 1050 that is displayed when the diabetes profile selection 1008 is selected in FIG. 10A. The diabetes profile screen 1050 includes a date of birth field 1052, a gender field 1054, a diabetes type field 1056 and an insulin information field 1058. The fields 1052, 1054, 1056 and 1058 allow a user to adjust their profile for diagnosis and planning.

Figure 11A:
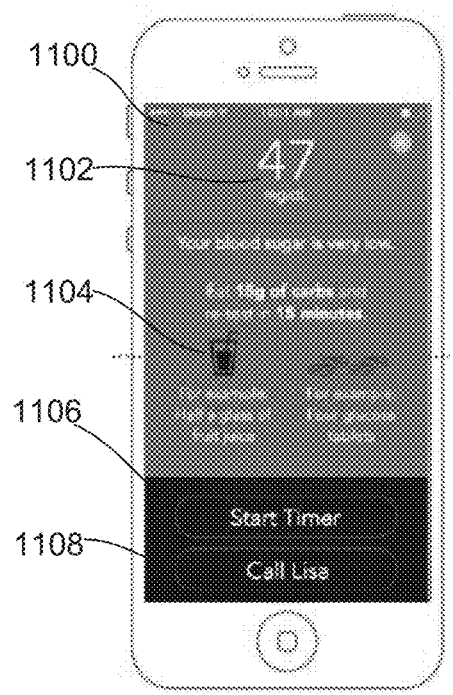
FIG. 11A illustrates a warning screen indicating a critical condition for the mobile device in FIG. 1.

FIG. 11A is an example warning screen 1100 that is displayed when a condition is detected based on test data from the test sensor 110 that requires warning to the user. For example, the warning screen 1100 may pop up when a reading is above or below the target range by over a predetermined value indicating either a critically high or low reading. In the example shown in FIG. 11A, the concentration reading is critically low. The warning screen 1100 includes a reading field 1102 that shows the critically low reading. A warning message 1104 gives the user a description of the warning and a recommendation as to cure the low reading. In this example, the background color is red indicating that a critical low reading condition has occurred. Other colors such as orange may be used for a critically high measurement. A start timer button 1106 allows a user to set a timer to take another measurement to determine if the recommendation is followed. A call button 1108 activates the phone on the mobile device 130 and calls an emergency contact to assist the user.

Figure 11B:
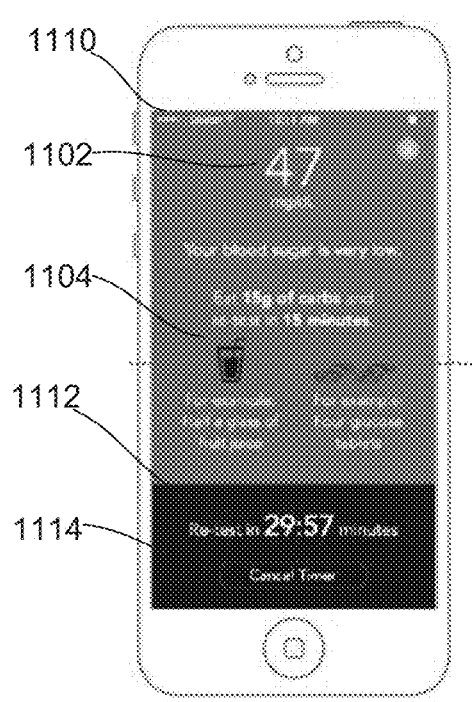
FIG. 11B illustrates a warning screen for a countdown for a follow up test for the mobile device in FIG. 1.

When the start timer button 1106 is activated, the warning screen shifts to a timer countdown display screen 1110 as shown in FIG. 11B. The countdown display screen retains the reading 1102 and warning information 1104 from the warning screen 1100 in FIG. 11A. The countdown screen 1110 includes a countdown time 1112 that shows the time to the next measurement. A cancel timer button 1114 allows a user to cancel the countdown.

Figure 11C:
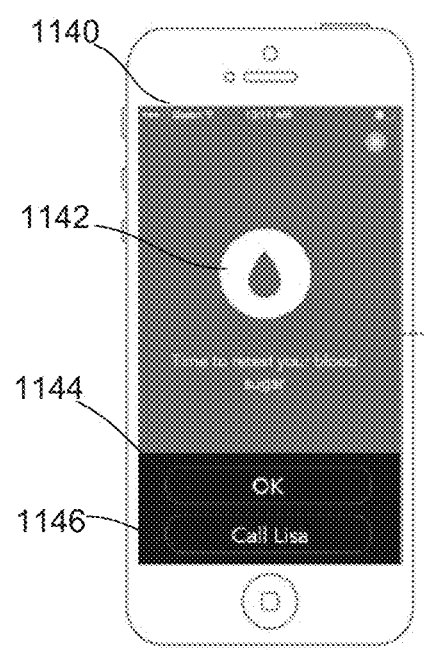
FIG. 11C illustrates a reminder screen to initiate a follow up test in response to a critical condition for the mobile device in FIG. 1.

When the counter reaches the time for a measurement, the display shows an alert screen 1140 shown in FIG. 11C. The alert screen 1140 includes an informational message and icon 1142 that tells the user to conduct a test. An OK button 1144 allows the user to acknowledge the alert. A call button 1108 activates the phone on the mobile device 130 and calls an emergency contact to assist the user. If the second test reading is within acceptable parameters, the application returns to normal operation.

Figure 11D:
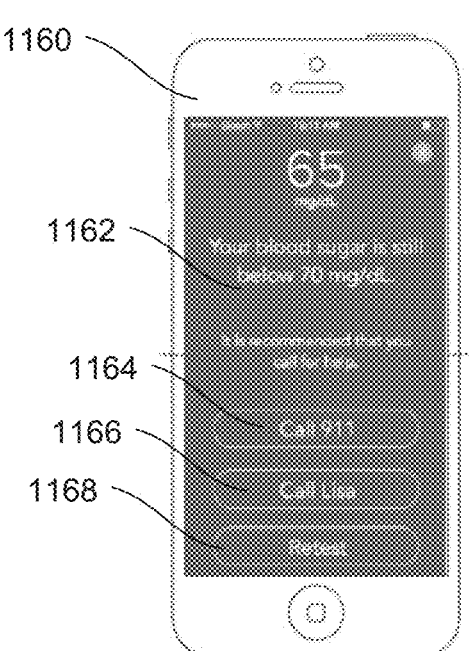
FIG. 11D illustrates a critical warning screen displayed after the critical condition is still present for the mobile device in FIG. 1.

If the second test reading remains in the critical range, the application will display a critical warning screen 1160 as shown in FIG. 11D. The critical warning screen 1160 includes an information area 1162 that contains the new reading and a warning that the reading is still in the critical range. The screen 1160 includes a call 911 button 1164 that automatically calls emergency services. The screen 1160 also includes a call button 1166 activates the phone on the mobile device 130 and calls an emergency contact to assist the user. Finally, the screen 1160 includes a retest button 1168 that indicates that the user will retest using the testing device 110.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What we claim is:

1. A system for managing health data, comprising:
a control meter configured to receive a glucose data signal from a continuous glucose monitor sensor;
a testing device comprising a first wireless transceiver configured to receive the glucose data signal from the control meter and to transmit glucose data to a mobile device, the glucose data based at least in part on the glucose data signal;
a mobile device, the mobile device comprising:
at least one processor,
a memory device,
a second wireless transceiver, and
a display;
wherein the memory device comprises non-transitory computer-executable instructions that, when executed by the at least one processor, cause the mobile device to:
communicate via the second wireless transceiver to the first wireless transceiver of the testing device to activate a pairing of the mobile device with the testing device;
cause the testing device to transmit the glucose data via the first wireless transceiver to the second wireless transceiver and cause the second wireless transceiver to receive the glucose data from the first wireless transceiver;
analyze the glucose data and determine, based at least in part on the glucose data, a plurality of behavior patterns associated with a user,
wherein each behavior pattern of the plurality of behavior patterns comprises one or more actions or choices made by the user during a pre-determined time period leading up to a glucose level measurement;
determine and select from among the plurality of behavior patterns, a subset of behavior patterns, the subset of behavior patterns comprising a first behavior pattern and a second behavior pattern, wherein the first behavior pattern are actions associated with calculated glucose level measurements within an acceptable range and wherein the second behavior pattern are actions or choices associated with calculated glucose level measurements outside the acceptable range;
assign a first category and a first status to each of the first behavior pattern and the second behavior pattern;
cause the display of the mobile device to provide a visual representation comprising a first indication and a second indication, the first indication indicating the first behavior pattern, that the first behavior pattern is beneficial, and that the user should repeat the actions associated with the first behavior pattern, and the first category and the first status associated with the first behavior pattern and the second indication indicating the second behavior pattern, that the second behavior pattern is problematic, a recommended corrective action second behavior pattern, and the first category and the first status of the second behavior pattern,
wherein the recommended corrective action includes a recommendation to avoid actions associated with the second behavior pattern; and
responsive to receiving an input from the user, update the first category or the first status of either the first behavior pattern or the second behavior pattern.

2. The system of claim 1, wherein the mobile device comprises a network transmitter, and wherein the non-transitory computer-executable instructions, when executed by the at least one processor, cause the network transmitter to send the glucose data to a cloud server.

3. The system of claim 1, wherein the pairing is activated responsive to a physical tap between the testing device and the mobile device, wherein the physical tap is sensed by the testing device and the mobile device, and wherein the testing device and the mobile device are configured to determine that the physical tap represents an intention to pair the testing device and the mobile device.

4. The system of claim 1, wherein the second behavior pattern comprises at least one of: high or low readings after a specific meal, high or low readings before a specific meal, lack of consistent testing frequency, lack of consistent testing at a set time, low frequency of testing, high or low readings at a particular time, approaching critical high or low readings consistently, or high or low days of week.

5. The system of claim 1, wherein the non-transitory computer-executable instructions, when executed by the at least one processor, cause the mobile device to:
generate a warning when the glucose data indicate that a glucose level falls outside selected glucose parameters for the user.

6. The system of claim 1, wherein the non-transitory computer-executable instructions, when executed by the at least one processor, cause the mobile device to:
analyze the glucose data and historical data pertaining to the user to determine a pattern of glucose levels for the user over a predetermined time period, wherein the plurality of behavior patterns are determined based at least in part on the pattern of glucose levels.

7. The system of claim 6, wherein the non-transitory computer-executable instructions, when executed by the at least one processor, cause the mobile device to:
display a warning icon on the display indicating that one of the behavior patterns from among the subset of behavior patterns has not been read by the user.

8. A method for managing health data, the method comprising:
determining, via at least one processor of a mobile device, a plurality of behavior patterns associated with a user of a continuous glucose monitoring sensor, the plurality of behavior patterns based at least in part on glucose data transmitted to the mobile device from a testing device based at least in part on signals from the continuous glucose monitoring sensor transmitted to the testing device,
wherein each behavior pattern of the plurality of behavior patterns comprises one or more actions or choices made by the user during a pre-determined time period leading up to a glucose level measurement;
determining and selecting, via the at least one processor, a subset of behavior patterns from among the plurality of behavior patterns, the subset of behavior patterns comprising a first behavior pattern and a second behavior pattern, wherein the first behavior pattern are actions associated with calculated glucose level measurements within an acceptable range and wherein the second behavior pattern are actions or choices associated with calculated glucose level measurements outside the acceptable range;

assigning a first category and a first status to each of the first behavior pattern and the second behavior pattern;

causing, via the at least one processor, a display of the mobile device to provide a visual representation comprising a first indication and a second indication;

wherein the first indication indicates the first behavior pattern, that the first behavior pattern is beneficial, and that the user should repeat the actions associated with the first behavior pattern, and the first category and the first status associated with the first behavior pattern;

wherein the second indication indicates the second behavior pattern, that the second behavior pattern is problematic, and a recommended corrective action for the second behavior pattern, and the first category and the first status of the second behavior pattern, wherein the recommended corrective action includes a recommendation to avoid actions associated with the second behavior pattern; and responsive to receiving an input from the user, updating the first category or the first status of either the first behavior pattern or the second behavior pattern.

9. The method of claim 8, comprising:
causing, via the at least one processor, a network transmitter of the mobile device to transmit the glucose data to a cloud server.

10. The method of claim 8, comprising:
causing, via the at least one processor, a pairing of the mobile device with the testing device;
causing, via the at least one processor, a wireless transceiver of the mobile device to provide a prompt to the testing device to transmit the glucose data to the wireless transceiver of the mobile device; and
causing, via the at least one processor, the wireless transceiver of the mobile device to receive the glucose data from the testing device;
wherein the pairing caused via the at least one processor is activated responsive to a physical tap between the testing device and the mobile device, wherein the physical tap is sensed by the testing device and the mobile device, and wherein the testing device and the mobile device are configured to determine that the physical tap represents an intention to pair the testing device and the mobile device.

11. The method of claim 8, wherein the second behavior pattern comprises at least one of: high or low readings after a specific meal, high or low readings before a specific meal, lack of consistent testing frequency, lack of consistent testing at a set time, low frequency of testing, high or low readings at a particular time, approaching critical high or low readings consistently, or high or low days of week.

12. The method of claim 8, further comprising:
causing, via the at least one processor, the display of the mobile device to display a warning indicating that at least one of the behavior patterns from among the subset of behavior patterns has not been observed by the user.

13. The method of claim 8, further comprising:
analyzing, via the at least one processor, the glucose data and historical data pertaining to the user to determine a pattern of glucose levels for the user over a predetermined time period, wherein the plurality of behavior patterns are determined based at least in part on the pattern of glucose levels.

14. A mobile device for managing health data, the mobile device comprising:
at least one processor;
a memory device;
a wireless transceiver; and
a display;
wherein the memory device comprises non-transitory computer-executable instructions that, when executed by the at least one processor, cause the mobile device to:
communicate via the wireless transceiver with a testing device to pair the mobile device with the testing device;
prompt the testing device to transmit glucose data to the wireless transceiver and cause the wireless transceiver to receive the glucose data from the testing device;
determine, based at least in part on an analysis of the glucose data, a plurality of behavior patterns associated with a user,
wherein each behavior pattern of the plurality of behavior patterns comprises one or more actions or choices made by the user during a pre-determined time period leading up to a glucose level measurement;
determine and select from among the plurality of behavior patterns, a subset of behavior patterns, the subset of behavior patterns comprising a first behavior pattern and a second behavior pattern, wherein the first behavior pattern are actions associated with calculated glucose level measurements within an acceptable range and wherein the second behavior pattern are actions or choices associated with calculated glucose level measurements outside the acceptable range;
assign a first category and a first status to each of the first behavior pattern and the second behavior pattern;
cause the display to provide a visual representation comprising a first indication and a second indication;
wherein the first indication indicates the first behavior pattern, that the first behavior pattern is beneficial, that the user should repeat the actions associated with the first behavior pattern, and the first category and the first status of the second behavior pattern,
wherein the second indication indicates the second behavior pattern, that the second behavior pattern is problematic, a recommended corrective action for the second behavior pattern, and the first category and the first status of the second behavior pattern,
wherein the recommended corrective action includes a recommendation to avoid actions associated with the second behavior pattern; and
responsive to receiving an input from the user, update the first category or the first status of either the first behavior pattern or the second behavior pattern.

15. The mobile device of claim 14, wherein the second behavior pattern comprises at least one of: high or low readings after a specific meal, high or low readings before a specific meal, lack of consistent testing frequency, lack of consistent testing at a set time, low frequency of testing, high or low readings at a particular time, approaching critical high or low readings consistently, or high or low days of week.

16. The mobile device of claim 14, wherein the plurality of behavior patterns is determined based at least in part on a pattern of glucose levels.

17. The mobile device of claim 14, wherein the visual representation further comprises a warning icon indicating that one of the behavior patterns from among the subset of behavior patterns has not been read by the user.

18. The mobile device of claim 14, wherein the visual representation comprises a warning when the glucose data indicate that a glucose level falls outside selected glucose parameters for the user.

* * * * *